(12) United States Patent
Sczepanski et al.

(10) Patent No.: US 12,203,068 B2
(45) Date of Patent: Jan. 21, 2025

(54) HETEROCHIRAL NUCLEIC ACID STRAND-DISPLACEMENT SYSTEMS AND METHODS

(71) Applicant: The Texas A&M University System, College Station, TX (US)

(72) Inventors: Jonathan T. Sczepanski, College Station, TX (US); Adam M. Kabza, Bryan, TX (US); Brian E. Young, College Station, TX (US)

(73) Assignee: The Texas A&M University System, College Station, TX (US)

( * ) Notice: Subject to any disclaimer, the term of this patent is extended or adjusted under 35 U.S.C. 154(b) by 1200 days.

(21) Appl. No.: 16/967,131

(22) PCT Filed: Feb. 4, 2019

(86) PCT No.: PCT/US2019/016502
§ 371 (c)(1),
(2) Date: Aug. 4, 2020

(87) PCT Pub. No.: WO2019/152919
PCT Pub. Date: Aug. 8, 2019

(65) Prior Publication Data
US 2021/0222250 A1 Jul. 22, 2021

Related U.S. Application Data

(60) Provisional application No. 62/626,124, filed on Feb. 4, 2018.

(51) Int. Cl.
| | | |
|---|---|---|
| C07H 21/04 | (2006.01) |
| C12N 15/11 | (2006.01) |
| C12N 15/115 | (2010.01) |
| C12Q 1/6825 | (2018.01) |
| C12Q 1/6886 | (2018.01) |
| G01N 21/64 | (2006.01) |

(52) U.S. Cl.
CPC ............ *C12N 15/11* (2013.01); *C12N 15/115* (2013.01); *C12Q 1/6825* (2013.01); *C12Q 1/6886* (2013.01); *G01N 21/6428* (2013.01); *C12Q 2537/1373* (2013.01); *C12Q 2600/158* (2013.01); *G01N 2021/6439* (2013.01)

(58) Field of Classification Search
None
See application file for complete search history.

(56) References Cited

U.S. PATENT DOCUMENTS

2017/0275621 A1   9/2017   Butler et al.

OTHER PUBLICATIONS

Kabza, Adam M. et al.; "Heterochiral DNA Strand-Displacement Circuits"; Journal of the American Chemical Society; vol. 139; 2017; pp. 17715-17718.

*Primary Examiner* — Kimberly Chong
(74) *Attorney, Agent, or Firm* — Winstead PC

(57) ABSTRACT

In an embodiment, a strand displacement system including a DNA/PNA complex, an input DNA strand, where the DNA/PNA complex binds to the input DNA strand forming a complex and displaces a PNA intermediate and forms an activated domain on the PNA, and a Bi complex that reacts with the activated domain on the PNA to thereby release an output DNA strand. In an additional embodiment, a fluorogenic sensor including a heteroduplex between an achiral PNA strand and a fluorogenic aptamer, where the fluorogenic aptamer includes L-RNA, an input DNA strand, where the input DNA strand binds to the heteroduplex and displaces an incumbent fluorogenic aptamer strand and forms an activated domain on that strand, and a dye.

6 Claims, 10 Drawing Sheets
Specification includes a Sequence Listing.

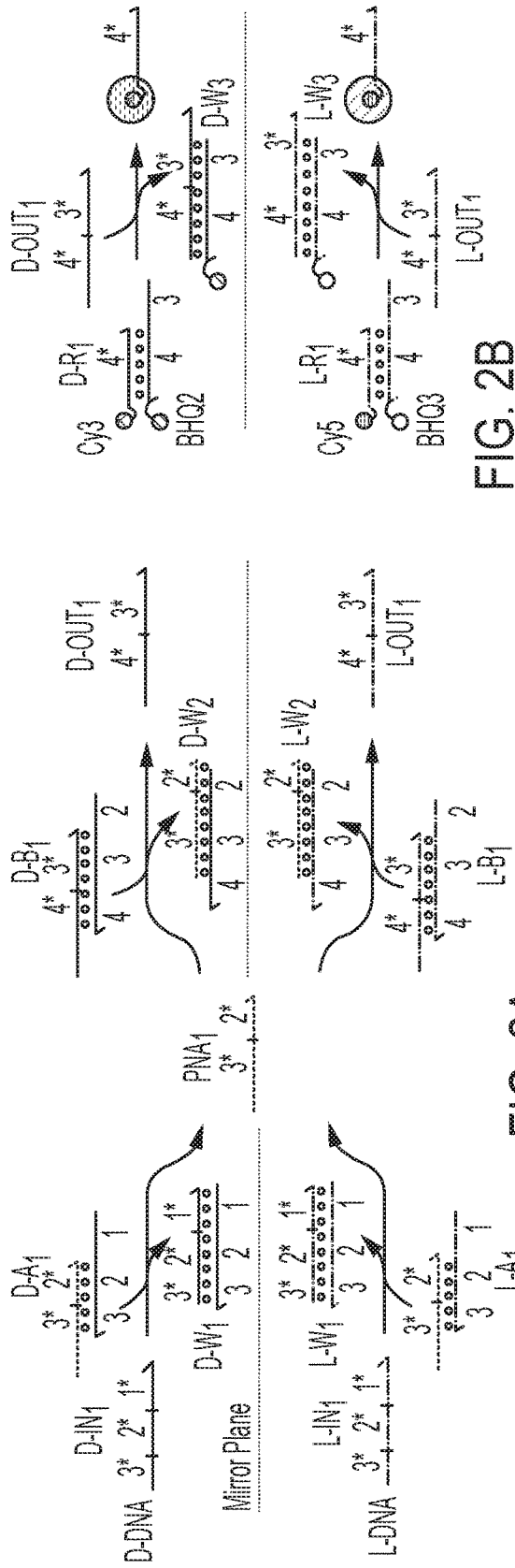
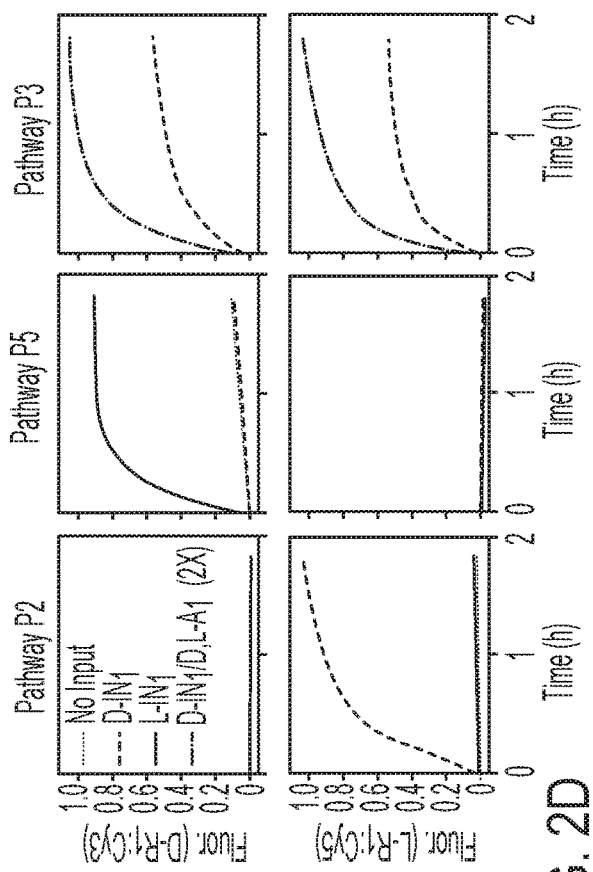
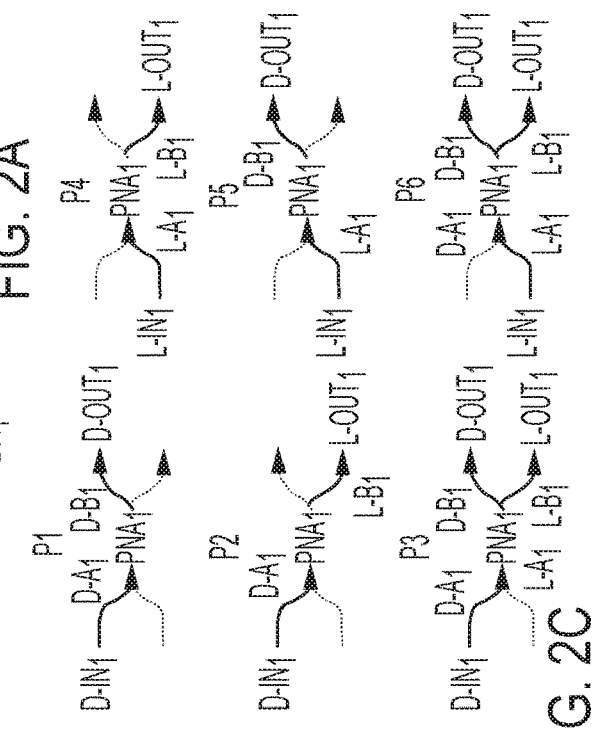
FIG. 2A
FIG. 2B
FIG. 2C
FIG. 2D

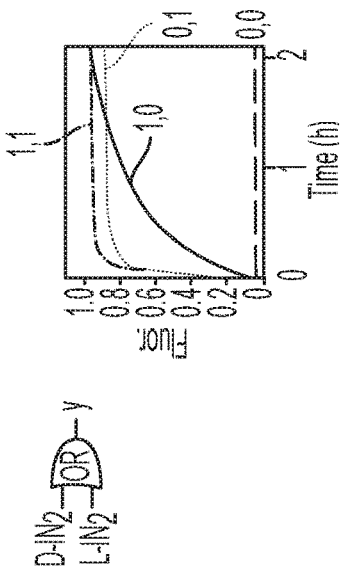
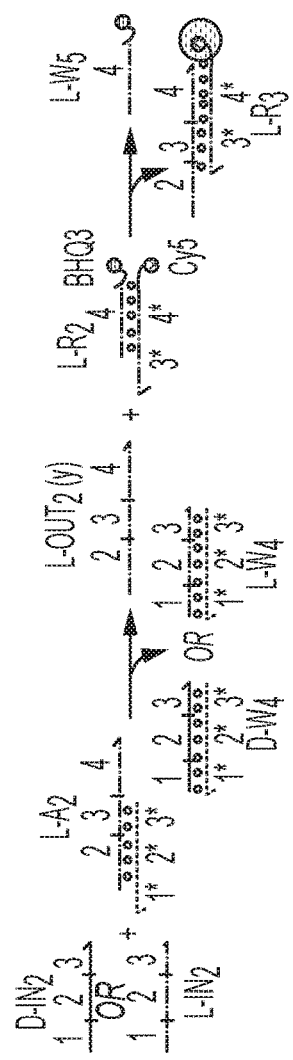
FIG. 3A
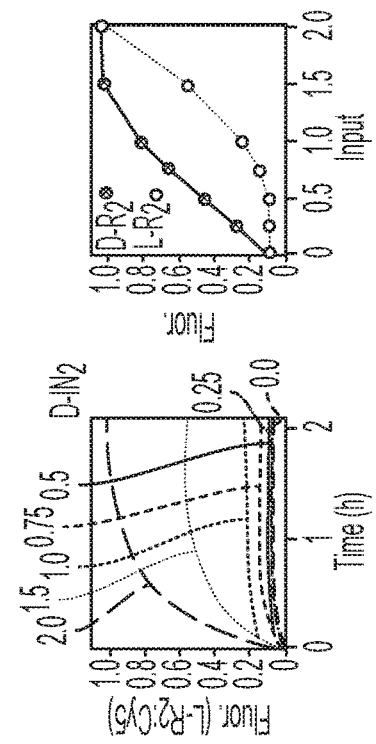
FIG. 3B
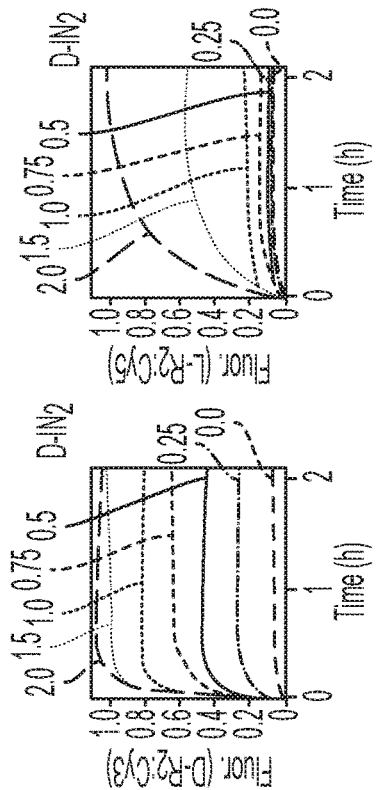
FIG. 3C
FIG. 3D
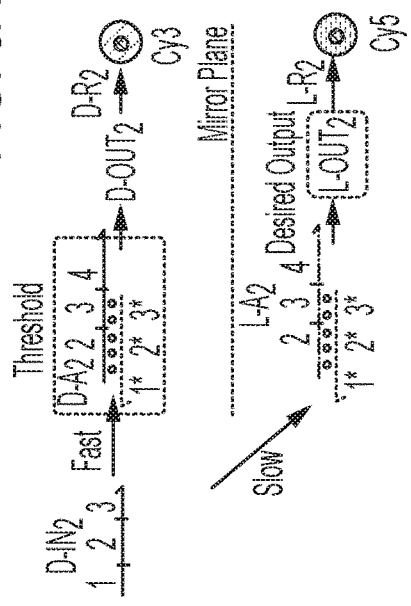
FIG. 3E
FIG. 3F

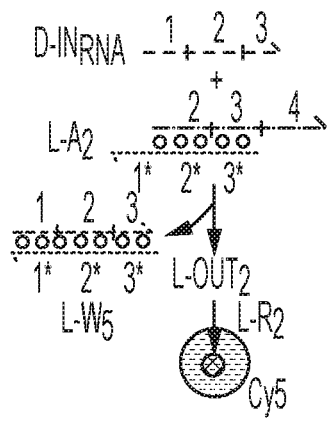 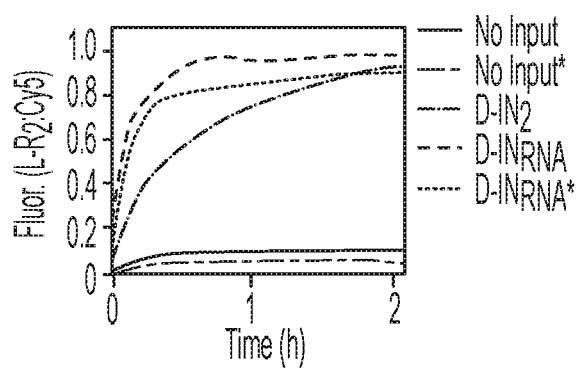
FIG. 4A      FIG. 4B
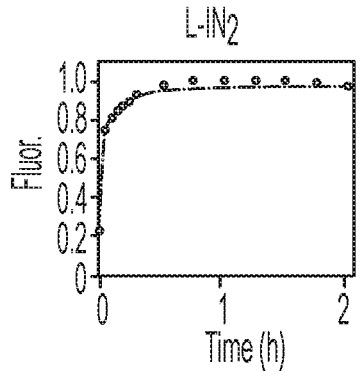 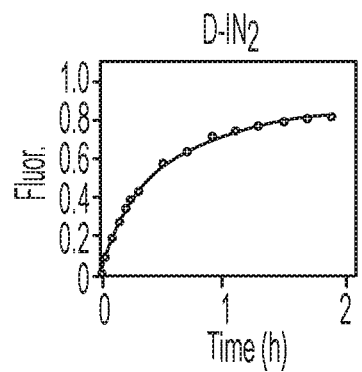 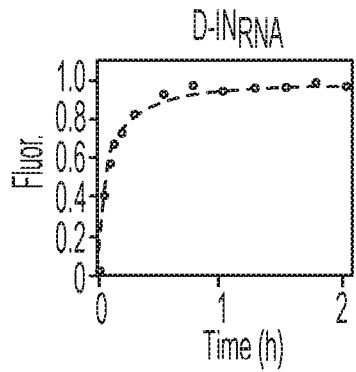
FIG. 5A      FIG. 5B      FIG. 5C
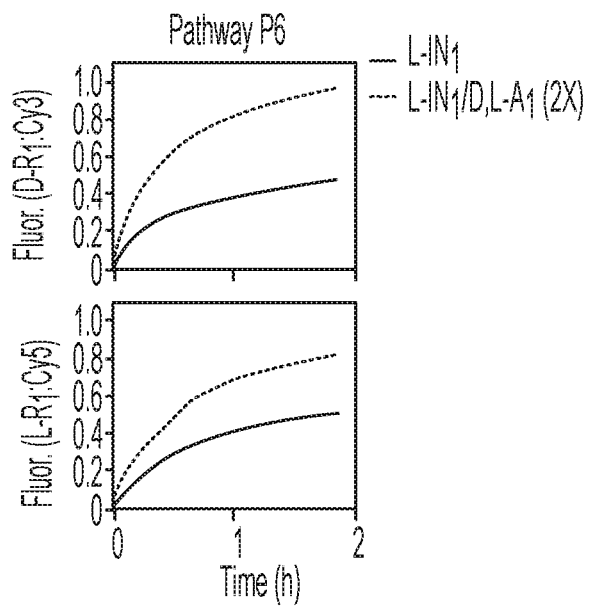
FIG. 6

```
                              SEQUENCE LISTING

<160> NUMBER OF SEQ ID NOS: 49

<210> SEQ ID NO 1
<211> LENGTH: 30
<212> TYPE: DNA
<213> ORGANISM: Artificial Sequence
<220> FEATURE:
<223> OTHER INFORMATION: Primer

<400> SEQUENCE: 1
ccctcattca ttcatctcca tagtgcacgg                                            30

<210> SEQ ID NO 2
<211> LENGTH: 24
<212> TYPE: DNA
<213> ORGANISM: Artificial Sequence
<220> FEATURE:
<223> OTHER INFORMATION: Primer

<400> SEQUENCE: 2
acatcatatt ccctcattca ttca                                                  24

<210> SEQ ID NO 3
<211> LENGTH: 30
<212> TYPE: DNA
<213> ORGANISM: Artificial Sequence
<220> FEATURE:
<223> OTHER INFORMATION: Primer

<400> SEQUENCE: 3
ccgtgcacta tggagatgaa tgaatgaggg                                            30

<210> SEQ ID NO 4
<211> LENGTH: 35
<212> TYPE: DNA
<213> ORGANISM: Artificial Sequence
<220> FEATURE:
<223> OTHER INFORMATION: Primer

<400> SEQUENCE: 4
gtatcttagt gtccattgca catcatattc cctca                                      35

<210> SEQ ID NO 5
<211> LENGTH: 29
<212> TYPE: DNA
<213> ORGANISM: Artificial Sequence
<220> FEATURE:
<223> OTHER INFORMATION: Primer

<400> SEQUENCE: 5
tgaatgaatg agggaatatg atgtgcaat                                             29

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
gtatcttagt gtccattgca                                                       20
```

<210> SEQ ID NO 7
<211> LENGTH: 26
<212> TYPE: DNA
<213> ORGANISM: Artificial Sequence
<220> FEATURE:
<223> OTHER INFORMATION: Primer

<400> SEQUENCE: 7
atgatgtgca atggacacta agatac                                          26

<210> SEQ ID NO 8
<211> LENGTH: 30
<212> TYPE: DNA
<213> ORGANISM: Artificial Sequence
<220> FEATURE:
<223> OTHER INFORMATION: Primer

<400> SEQUENCE: 8
ccctcattca ttcatctcca tagtgcacgg                                      30

<210> SEQ ID NO 9
<211> LENGTH: 30
<212> TYPE: DNA
<213> ORGANISM: Artificial Sequence
<220> FEATURE:
<223> OTHER INFORMATION: Primer

<400> SEQUENCE: 9
ccgtgcacta tggagatgaa tgaatgaggg                                      30

<210> SEQ ID NO 10
<211> LENGTH: 35
<212> TYPE: DNA
<213> ORGANISM: Artificial Sequence
<220> FEATURE:
<223> OTHER INFORMATION: Primer

<400> SEQUENCE: 10
gtatcttagt gtccattgca catcatattc cctca                                35

<210> SEQ ID NO 11
<211> LENGTH: 29
<212> TYPE: DNA
<213> ORGANISM: Artificial Sequence
<220> FEATURE:
<223> OTHER INFORMATION: Primer

<400> SEQUENCE: 11
tgaatgaatg agggaatatg atgtgcaat                                       29

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
gtatcttagt gtccattgca                                                 20

<210> SEQ ID NO 13
<211> LENGTH: 26
<212> TYPE: DNA
<213> ORGANISM: Artificial Sequence
<220> FEATURE:

<223> OTHER INFORMATION: Primer

<400> SEQUENCE: 13
atgatgtgca atggacacta agatac                                    26

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
ttaatgctaa tcgtgatagg                                           20

<210> SEQ ID NO 15
<211> LENGTH: 28
<212> TYPE: DNA
<213> ORGANISM: Artificial Sequence
<220> FEATURE:
<223> OTHER INFORMATION: Primer

<400> SEQUENCE: 15
ctaatcgtga taggatcgaa ctggtacg                                  28

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
ttaatgctaa tcgtgatagg                                           20

<210> SEQ ID NO 17
<211> LENGTH: 28
<212> TYPE: DNA
<213> ORGANISM: Artificial Sequence
<220> FEATURE:
<223> OTHER INFORMATION: Primer

<400> SEQUENCE: 17
ctaatcgtga taggatcgaa ctggtacg                                  28

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
cctatcacga ttagcattaa                                           20

<210> SEQ ID NO 19
<211> LENGTH: 22
<212> TYPE: DNA
<213> ORGANISM: Artificial Sequence
<220> FEATURE:
<223> OTHER INFORMATION: Primer

<400> SEQUENCE: 19
ggcgtaccag ttcgatccta tc                                        22

```
<210> SEQ ID NO 20
<211> LENGTH: 16
<212> TYPE: DNA
<213> ORGANISM: Artificial Sequence
<220> FEATURE:
<223> OTHER INFORMATION: Primer

<400> SEQUENCE: 20
atcgaactgg tacgcc                                                         16

<210> SEQ ID NO 21
<211> LENGTH: 22
<212> TYPE: DNA
<213> ORGANISM: Artificial Sequence
<220> FEATURE:
<223> OTHER INFORMATION: Primer

<400> SEQUENCE: 21
ggcgtaccag ttcgatccta tc                                                  22

<210> SEQ ID NO 22
<211> LENGTH: 16
<212> TYPE: DNA
<213> ORGANISM: Artificial Sequence
<220> FEATURE:
<223> OTHER INFORMATION: Primer

<400> SEQUENCE: 22
atcgaactgg tacgcc                                                         16

<210> SEQ ID NO 23
<211> LENGTH: 23
<212> TYPE: RNA
<213> ORGANISM: Artificial Sequence
<220> FEATURE:
<223> OTHER INFORMATION: Primer

<400> SEQUENCE: 23
uuaaugcuaa ucgugauagg ggu                                                 23

<210> SEQ ID NO 24
<211> LENGTH: 82
<212> TYPE: DNA
<213> ORGANISM: Artificial Sequence
<220> FEATURE:
<223> OTHER INFORMATION: Primer

<400> SEQUENCE: 24
taatacgact cactataggg gcacgtacga aggaaggatt ggtaggcacg tacgaatata         60
ccacatacca atccttcctt cg                                                  82

<210> SEQ ID NO 25
<211> LENGTH: 84
<212> TYPE: DNA
<213> ORGANISM: Artificial Sequence
<220> FEATURE:
<223> OTHER INFORMATION: Primer

<400> SEQUENCE: 25
taatacgact cactatagga atcgtgatag gcgaaggaag gattgatagg cgaatatacc         60
acataccaat ccttccttcg ccta                                                84

<210> SEQ ID NO 26
<211> LENGTH: 76
<212> TYPE: DNA
```

```
<213> ORGANISM: Artificial Sequence
<220> FEATURE:
<223> OTHER INFORMATION: Primer

<400> SEQUENCE: 26
taatacgact cactatagga atcgtgatag gggaaggatt gataggcgaa tataccacat    60
accaatcctt ccccta                                                   76

<210> SEQ ID NO 27
<211> LENGTH: 80
<212> TYPE: DNA
<213> ORGANISM: Artificial Sequence
<220> FEATURE:
<223> OTHER INFORMATION: Primer

<400> SEQUENCE: 27
taatacgact cactatagga atcgtgatag gcgaaggaag gattggcgaa tataccacat    60
accaatcctt ccttcgccta                                               80

<210> SEQ ID NO 28
<211> LENGTH: 76
<212> TYPE: DNA
<213> ORGANISM: Artificial Sequence
<220> FEATURE:
<223> OTHER INFORMATION: Primer

<400> SEQUENCE: 28
taatacgact cactataggt aatcgtgata ggaaggattc gtgatatata ccacatacca    60
atccttccta tcacga                                                   76

<210> SEQ ID NO 29
<211> LENGTH: 46
<212> TYPE: RNA
<213> ORGANISM: Artificial Sequence
<220> FEATURE:
<223> OTHER INFORMATION: Primer

<400> SEQUENCE: 29
ggcacguacg aaggaaggau ugguaugugg uauauucgua cgugcc                  46

<210> SEQ ID NO 30
<211> LENGTH: 50
<212> TYPE: RNA
<213> ORGANISM: Artificial Sequence
<220> FEATURE:
<223> OTHER INFORMATION: Primer

<400> SEQUENCE: 30
ggaaucguga uaggcgaagg aaggauuggu augugguaua uucgccuauc              50

<210> SEQ ID NO 31
<211> LENGTH: 44
<212> TYPE: RNA
<213> ORGANISM: Artificial Sequence
<220> FEATURE:
<223> OTHER INFORMATION: Primer

<400> SEQUENCE: 31
ggaaucguga uaggaaggaa ggauuggu augugguauauu ccua                    44

<210> SEQ ID NO 32
<211> LENGTH: 46
<212> TYPE: RNA
<213> ORGANISM: Artificial Sequence
```

```
<220> FEATURE:
<223> OTHER INFORMATION: Primer

<400> SEQUENCE: 32
ggaaucguga uaggcgaagg aaggauuggu augugguaua uucgcc          46

<210> SEQ ID NO 33
<211> LENGTH: 42
<212> TYPE: RNA
<213> ORGANISM: Artificial Sequence
<220> FEATURE:
<223> OTHER INFORMATION: Primer

<400> SEQUENCE: 33
gguaaucgug auaggaagga uugguaugug guauauauca cg              42

<210> SEQ ID NO 34
<211> LENGTH: 19
<212> TYPE: DNA
<213> ORGANISM: Artificial Sequence
<220> FEATURE:
<223> OTHER INFORMATION: Primer

<400> SEQUENCE: 34
ctatcacgat tagcattaa                                        19

<210> SEQ ID NO 35
<211> LENGTH: 40
<212> TYPE: RNA
<213> ORGANISM: Artificial Sequence
<220> FEATURE:
<223> OTHER INFORMATION: Primer

<400> SEQUENCE: 35
uaaucgugau aggaaggauu gguauguggu auauaucacg                 40

<210> SEQ ID NO 36
<211> LENGTH: 83
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (26)..(43)
<220> FEATURE:
<221> NAME/KEY: misc_feature
<222> LOCATION: (26)..(43)
<223> OTHER INFORMATION: n is a, c, g, t or u

<400> SEQUENCE: 36
tggatatcta aatgtacgt acggtnnnnn nnnnnnnnnn nnnuaaucgu gauaggaagg    60
auugguaugu gguauauauc acg                                          83

<210> SEQ ID NO 37
<211> LENGTH: 25
<212> TYPE: DNA
<213> ORGANISM: Artificial Sequence
<220> FEATURE:
<223> OTHER INFORMATION: Primer

<400> SEQUENCE: 37
accgtacgta cattctagat atcca                                 25

<210> SEQ ID NO 38
<211> LENGTH: 24
```

```
<212> TYPE: RNA
<213> ORGANISM: Artificial Sequence
<220> FEATURE:
<223> OTHER INFORMATION: Primer

<400> SEQUENCE: 38
uuggggauag ugcuaaucgu aauu                                          24

<210> SEQ ID NO 39
<211> LENGTH: 34
<212> TYPE: DNA
<213> ORGANISM: Artificial Sequence
<220> FEATURE:
<223> OTHER INFORMATION: Primer

<400> SEQUENCE: 39
tcgaggatcc tctctcttgc aggtggcaca aacc                               34

<210> SEQ ID NO 40
<211> LENGTH: 32
<212> TYPE: DNA
<213> ORGANISM: Artificial Sequence
<220> FEATURE:
<223> OTHER INFORMATION: Primer

<400> SEQUENCE: 40
tcgagctagc agtctaagtt tatccagcag gg                                 32

<210> SEQ ID NO 41
<211> LENGTH: 18
<212> TYPE: DNA
<213> ORGANISM: Artificial Sequence
<220> FEATURE:
<223> OTHER INFORMATION: Primer

<400> SEQUENCE: 41
gccaccatga ccgagtac                                                 18

<210> SEQ ID NO 42
<211> LENGTH: 22
<212> TYPE: DNA
<213> ORGANISM: Artificial Sequence
<220> FEATURE:
<223> OTHER INFORMATION: Primer

<400> SEQUENCE: 42
ggtgtgtcag aattcagatc tc                                            22

<210> SEQ ID NO 43
<211> LENGTH: 46
<212> TYPE: RNA
<213> ORGANISM: Artificial Sequence
<220> FEATURE:
<223> OTHER INFORMATION: Primer

<400> SEQUENCE: 43
ggcacguacg aaggaaggau ugguaugugg uauauucgua cgugcc                  46

<210> SEQ ID NO 44
<211> LENGTH: 48
<212> TYPE: RNA
<213> ORGANISM: Artificial Sequence
<220> FEATURE:
<223> OTHER INFORMATION: Primer

<400> SEQUENCE: 44
```

```
aaucgugaua ggcgaaggaa ggauuggguau gugguauauu cgccuauc                    48

<210> SEQ ID NO 45
<211> LENGTH: 42
<212> TYPE: RNA
<213> ORGANISM: Artificial Sequence
<220> FEATURE:
<223> OTHER INFORMATION: Primer

<400> SEQUENCE: 45
aaucgugaua ggaaggaagg auugguaugu gguauauucc ua                          42

<210> SEQ ID NO 46
<211> LENGTH: 44
<212> TYPE: RNA
<213> ORGANISM: Artificial Sequence
<220> FEATURE:
<223> OTHER INFORMATION: Primer

<400> SEQUENCE: 46
aaucgugaua ggcgaaggaa ggauuggguau gugguauauu cgcc                       44

<210> SEQ ID NO 47
<211> LENGTH: 40
<212> TYPE: RNA
<213> ORGANISM: Artificial Sequence
<220> FEATURE:
<223> OTHER INFORMATION: Primer

<400> SEQUENCE: 47
uaaucgugau aggaaggauu gguauguggu auauaucacg                             40

<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48
aattacgatt agcactatcc                                                   20

<210> SEQ ID NO 49
<211> LENGTH: 24
<212> TYPE: RNA
<213> ORGANISM: Artificial Sequence
<220> FEATURE:
<223> OTHER INFORMATION: Primer

<400> SEQUENCE: 49
uuaaugcuaa ucgugauagg gguu                                              24
```

HETEROCHIRAL NUCLEIC ACID STRAND-DISPLACEMENT SYSTEMS AND METHODS

CROSS-REFERENCE TO RELATED APPLICATIONS

This patent application claims priority from, and incorporates by reference the entire disclosure of, U.S. Provisional Patent Application No. 62/626,124 filed on Feb. 4, 2018.

TECHNICAL FIELD

The present disclosure relates generally to nucleic acid strand-displacement and more particularly, but not by way of limitation, to heterochiral nucleic acid strand-displacement systems and methods.

BACKGROUND

Due to the programmability offered by Watson-Crick base pairing rules, DNA has emerged as a leading material for the construction of nanoscale devices, including, but not limited to, logic circuits, molecular motors, and sensors. The ability of such devices to interact with cellular nucleic acids through simple hybridization forms the basis of an intense effort now underway to develop nucleic acid-based devices capable of analyzing and manipulating molecular information in living systems (i.e., "smart therapeutics"). Although recent work has begun to demonstrate the compatibility of nucleic acid nanodevices with complex biological environments, current technologies still suffer from two key limitations when applied to biological environments. In particular, natural nucleic acids are rapidly degraded by cellular nucleases, and oligonucleotides introduced exogenously into cells are susceptible to unintended interactions with cellular components, including off-target hybridization to native nucleic acids and triggering of the innate immune response. The present disclosure seeks to overcome these limitations.

The development of this invention was funded in part by the Welch Foundation under grant number A1909.

SUMMARY OF THE INVENTION

In an embodiment, a strand displacement system including a DNA/PNA complex, an input DNA strand, where the DNA/PNA complex binds to the input DNA strand forming a complex and displaces a PNA intermediate and forms an activated domain on the PNA, and a $B_1$ complex that reacts with the activated domain on the PNA to thereby release an output DNA strand.

In another embodiment, a method for strand-displacement including binding an input DNA strand to a DNA toehold domain of a DNA/PNA substrate, responsive to the binding, activating the DNA/PNA substrate, displacing an achiral PNA strand from the DNA/PNA substrate, and decoupling stereochemical information from a sequence present in the input DNA.

In a further embodiment, a chimeric DNA/PNA complex including an input strand, where the input strand binds to the chimeric DNA/PNA complex and releases an incumbent DNA strand and forms an activated domain on that strand, and a complex downstream $R_2$ that reacts with the activated domain on the released incumbent DNA strand.

In an additional embodiment, a fluorogenic sensor including a heteroduplex between an achiral PNA strand and a fluorogenic aptamer, where the fluorogenic aptamer includes L-RNA, an input strand, where the input strand binds to the heteroduplex and displaces an incumbent fluorogenic aptamer strand and forms an activated domain on that strand, and a dye.

In particular embodiment, a fluorogenic sensor including a heteroduplex between an achiral PNA strand and a Mango III aptamer including L-RNA, an input DNA strand of miRNA-155, wherein the miRNA-155 binds to the heteroduplex and displaces an incumbent Mango III aptamer strand and forms an activated domain on that strand, a dye including thiazole orange, and where fluorescent signaling is activated by proper folding of the Mango III aptamer as a result of displacement of the incumbent Mango III aptamer strand.

BRIEF DESCRIPTION OF THE DRAWINGS

A more complete understanding of the subject matter of the present disclosure may be obtained by reference to the following Detailed Description when taken in conjunction with the accompanying Drawings wherein:

FIG. 1 illustrates heterochiral DNA strand-displacement reactions.

FIG. 2 illustrates a heterochiral DNA strand-displacement circuit implemented with Reaction A. FIG. 2A shows a schematic illustration of the heterochiral circuit. FIG. 2B shows fluorescent reporter strategy. Domain 3* of the output strand from FIG. 2A (D-OUT$_1$ or L-OUT$_1$) will react with toehold domain 3 of the corresponding reporter complex (D-R$_1$ or L-R$_1$, respectively), displacing the incumbent fluorescent strand. FIG. 2C shows potential reaction pathways (P1-P6) for the circuit depicted in FIG. 2A. FIG. 2D shows a demonstration of the heterochiral circuit (pathways P2, P3, and P5). Reaction cascades contained 500 nM of the indicated circuit components, 300 mM NaCl, 1 mM EDTA, and 10 mM Tris (pH 7.6) and were carried out at 23° C. Reaction mixture also contained 500 nM of each reporter complex (D-R$_1$ and L-R$_1$) and their corresponding fluorescent signals were monitored in parallel. Fluorescence (Fluor.) is reported in units such that 1.0 is the fluorescence of the triggered reporter (in this case 500 nM) and 0.0 is the background of the quenched reporter complex.

FIG. 3 illustrates a heterochiral strand-displacement circuit implemented with Reaction B. FIG. 3A shows a schematic illustration of the chirality OR gate and associated reporter complex (L-R$_2$). FIG. 3B shows fluorescence monitoring (Cy5) of the chirality OR gate. FIG. 3C illustrates a "chirality threshold" gate built by combining both enantiomers of the A$_2$ heteroduplex, along with their corresponding reporter complexes, into a single reaction mixture. FIG. 3D illustrates thresholding (D-OUT$_2$) and production of the output signal (L-OUT$_2$) using reporter D-R$_2$ (Cy3). FIG. 3E illustrates thresholding (D-OUT$_2$) and production of the output signal (L-OUT$_2$) using reporter L-R$_2$ (Cy5). FIG. 3F shows that excess input signal (D-IN$_2$), relative to the threshold component (D-A$_2$), significant output signal produced (L-OUT$_2$), thereby confirming desirable thresholding behavior.

FIG. 4 illustrates that heterochiral strand-displacement circuits are capable of interfacing native D-RNA with L-DNA. FIG. 4A shows a schematic illustration of a heterochiral circuit that translates a natural D-RNA input signal into an L-DNA output signal. The components of this circuit, including the reporter complex, are identical to those used in FIG. 3A, however, an RNA version of D-IN$_2$ (D-IN$_{RNA}$) was used as the input strand. D-IN$_{RNA}$ is microRNA-155. FIG. 4B illustrates fluorescence monitoring (Cy5) of the heterochiral circuit in FIG. 4A. Reaction mixtures contained 500 nM of each circuit component, 300 mM NaCl, and 10 mM Tris (pH 7.6), and were carried out at 37° C. The asterisk indicates the presence of 0.1 mg/mL HeLa cell nuclear RNA extract.

FIG. 5 shows kinetic characterization of the heterochiral strand-displacement circuit depicted in FIG. 3A (chirality OR gate). Experimental data (dots) was fit to a second-order rate model (lines). Here, 1 fluorescence unit corresponds to the consumption of 500 nM L-R$_2$. Rate constants were calculated to be 2.14×10$^4$ M$^{-1}$ s$^{-1}$ in FIG. 5A, 9.56×10$^2$ M$^{-1}$ s$^{-1}$ in FIG. 5B, and 5.13×10$^3$ M$^{-1}$ s$^{-1}$ in FIG. 5C, for L-IN$_2$, D-IN$_2$, and D-IN$_{RNA}$, respectively.

FIG. 6 shows a demonstration of circuit pathway P6 of FIG. 2C. Reactions were carried out as described with respect to FIG. 2D (pathway P3) except that they were initiated with L-IN$_1$ in place of D-IN$_1$.

FIG. 9 illustrates design of a mirror-image fluorogenic aptamer sensor for detection of miRNAs in live cells.

FIG. 11 illustrates in vitro characterization of the pM-4 sensor.

FIG. 14 shows a schematic illustration of the cholesterol-conjugated sensors according to an embodiment of the present disclosure.

FIG. 16 illustrates detection of miRNA-155 in HeLa cells.

DETAILED DESCRIPTION

Figure 1A:
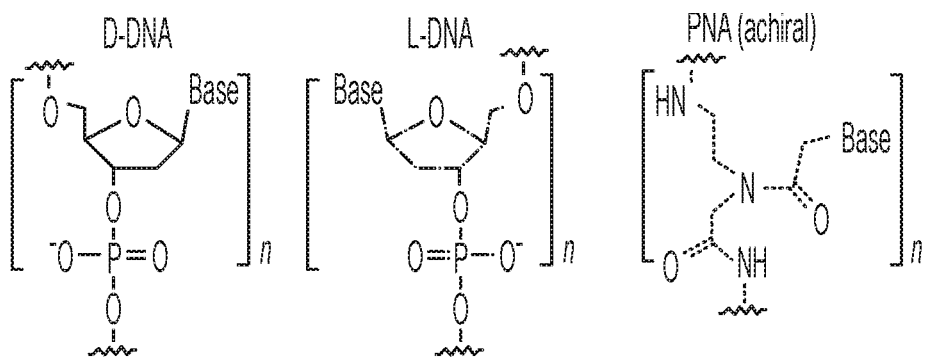
FIG. 1A illustrates the three types of nucleic acids according to an aspect of the present disclosure: D-DNA (solid line), L-DNA (dot-dash line), and PNA (dotted line).

It is to be understood that the following disclosure provides many different embodiments, or examples, for implementing different features of various embodiments. Specific examples of components and arrangements are described below to simplify the disclosure. These are, of course, merely examples and are not intended to be limiting. The section headings used herein are for organizational purposes and are not to be construed as limiting the subject matter described.

The absence of a straightforward strategy to interface native D-DNA with its enantiomer L-DNA—oligonucleotides of opposite chirality are incapable of forming contiguous Watson-Crick (WC) base pairs with each other—has enforced a "homochiral" paradigm over the field of dynamic DNA nanotechnology. As a result, chirality, a property of nucleic acids, is often overlooked as a design element for engineering DNA-based nanodevices and circuitry potentially limiting the types of behaviors that can be achieved using these systems. In an aspect of the present disclosure, discussed in further detail below, a toehold-mediated strand-displacement methodology for transferring information between orthogonal DNA enantiomers via an achiral intermediary is introduced, opening the door for "heterochiral" DNA nanotechnology having fully interfaced D-DNA and L-DNA components. On the basis of the approach disclosed herein, several heterochiral DNA circuits having various capabilities, including autonomous chiral inversion of DNA sequence information and chirality-based computing and thresholding are demonstrated. In addition, the present disclosure demonstrates that heterochiral circuits can directly interface endogenous RNAs, for example, microRNAs (miRNAs), with bioorthogonal L-DNA, suggesting applications in bioengineering and nanomedicine. Accordingly, chirality as a design parameter for engineering dynamic DNA can be realized using DNA.

Furthermore, development of biocompatible tools for intracellular imaging of miRNA expression remains challenging. As a result of the aforementioned heterochiral strand-displacement methodology, a further aspect of the present disclosure pertains generally to the use of heterochiral strand-displacement to sequence-specifically interface endogenous D-miRNAs with an L-RNA version of the fluorogenic aptamer Mango III, thereby generating a class of biocompatible miRNA sensors. Fluorescence activation of the sensor is achieved through the displacement of an achiral blocking strand from the L-Mango aptamer by the D-RNA target, as will be discussed in further detail below. In contrast to D-Mango, the present disclosure shows that the L-Mango sensor retains full functionality in serum, enabling a light-up fluorescence response to the target. A self-delivering version of the L-Mango sensor is employed to image the expression of microRNA-155 in living cells, representing the first time L-oligonucleotides have been interfaced with a living system. The present disclosure provides a new paradigm for the development of biocompatible hybridization-based sensors for live-cell imaging of RNAs and can expand the utility of fluorogenic aptamers for cellular applications.

Working Examples

Reference will now be made to more specific embodiments of the present disclosure and data that provides support for such embodiments. However, it should be noted that the disclosure below is for illustrative purposes only and is not intended to limit the scope of the claimed subject matter in any way.

Dynamic DNA devices almost invariably represent homochiral systems exclusively comprised of D-DNA, the naturally occurring stereoisomer, as shown in FIG. 1A. This is despite L-DNA, the enantiomer of D-DNA, having identical physical properties in terms of solubility, hybridization kinetics, and duplex thermal stability. A challenge associated with integrating both enantiomers of DNA into a single device is their inability to form WC base pairs with each other. While this property alone can be beneficial, especially for applications related to biotechnology, it precludes the sequence-specific transfer of information between the two enantiomers of DNA, thus undermining the interfaced (or heterochiral) construction sought. It is reasoned that this limitation could be overcome by employing an achiral nucleic acid analog as a sequence-specific mediator between the two orthogonal enantiomers of DNA. Therefore, an aspect of the present disclosure was drawn to peptide nucleic acid (PNA).

Oligonucleotides were either purchased from Integrated DNA Technologies (Coralville, IA) or prepared by solid-phase synthesis on an Expedite 8909 DNA/RNA synthesizer. DNA synthesis reagents and D-nucleoside phosphoramidites were purchased from Glen Research (Sterling, VA), and L-nucleoside phosphoramidites were purchased from ChemGenes (Wilmington, MA). Black Hole Quencher 2 (BHQ2) and Black Hole Quencher 3 (BHQ3) CPG resins were purchased from LGC Biosearch Technologies (Petaluma, CA). [Gamma-$^{32}$P]ATP was purchased from Perkin Elmer (Waltham, MA). Fluorescent dyes (NHS Cy3 and NHS Cy5) were purchased from Lumiprobe Life Science Solutions (Hallendale Beach, FL). Peptide nucleic acids (PNAs) were purchased from PNA Bio Inc. (Newbury Park, CA) at 99.9% purity and were not purified further.

DNA sequences, shown below in Table 1, for the strand-displacement circuit depicted in FIG. 2A were rationally designed and analyzed using NUPACK to ensure proper hybridization and eliminate spurious secondary structures. In particular, PNA$_1$ was designed to minimize the number of purine residues in order to ensure adequate solubility in aqueous media. The circuit depicted in FIG. 3A and FIG. 4A was designed around the sequence of microRNA-155 (D-IN$_{RNA}$; Table 1, shown below). The PNA sequence was chosen to be complementary to the 5' end of the microRNA, while the L-DNA and D-DNA strands, as well as reporter complexes, were rationally designed and verified via NUPACK. PNA melting temperatures were approximated using the PNA Tool from PNA Bio Inc. All DNA melting temperatures were approximated using the IDT Oligo Analyzer tool, utilizing the nearest neighbor approximation.

Table 1, shown below, illustrates names, sequences, and chirality of strands used according to an aspect of the present disclosure. For strands not named in the main text figures, they are named below based upon the complex they are associated with before initiation of the reaction, followed by their sequence domains listed in the 5'→3' direction (in parentheses). For example, strand D-B$_1$(2-3-4) is the bottom strand of complex D-B$_1$, illustrated in FIG. 2A.

TABLE 1

| Sequence Name | Sequence Identity 5' → 3' | Oligomer Stereochemistry |
| --- | --- | --- |
| D-IN$_1$ SEQ ID NO. 1 | CCCTCATTCATTCATCTCCATAGTGCACGG | D |
| PNA$_1$ SEQ ID NO. 2 | ACATCATATTCCCTCATTCATTCA | achiral |
| D-A$_1$(1-2-3) SEQ ID NO. 3 | CCGTGCACTATGGAGATGAATGAATGAGGG | D |
| D-OUT$_1$ SEQ ID NO. 4 | GTATCTTAGTGTCCATTGCACATCATATTCCCTCAD | D |
| D-B$_1$(2-3-4) SEQ ID NO. 5 | TGAATGAATGAGGGAATATGATGTGCAAT | D |
| D-R$_1$(4*) SEQ ID NO. 6 | Cy3-GTATCTTAGTGTCCATTGCA | D |

TABLE 1-continued

| Sequence Name | Sequence Identity 5' → 3' | Oligomer Stereochemistry |
|---|---|---|
| D-$R_1$(3-4) SEQ ID NO. 7 | ATGATGTGCAATGGACACTAAGATAC-BHQ2 | D |
| L-$IN_1$ SEQ ID NO. 8 | CCCTCATTCATTCATCTCCATAGTGCACGG | L |
| L-$A_1$(1-2-3) SEQ ID NO. 9 | CCGTGCACTATGGAGATGAATGAATGAGGG | L |
| L-$OUT_1$ SEQ ID NO. 10 | GTATCTTAGTGTCCATTGCACATCATATTCCCTCAL | L |
| L-$B_1$(2-3-4) SEQ ID NO. 11 | TGAATGAATGAGGGAATATGATGTGCAAT | L |
| L-$R_1$(4*) SEQ ID NO. 12 | Cy5-GTATCTTAGTGTCCATTGCA | L |
| L-$R_1$(3-4) SEQ ID NO. 13 | ATGATGTGCAATGGACACTAAGATAC-BHQ3 | L |
| D-$IN_2$ SEQ ID NO. 14 | TTAATGCTAATCGTGATAGG | D |
| D-$OUT_2$ SEQ ID NO. 15 | CTAATCGTGATAGGATCGAACTGGTACG | D |
| L-$IN_2$ SEQ ID NO. 16 | TTAATGCTAATCGTGATAGG | L |
| L-$OUT_2$ SEQ ID NO. 17 | CTAATCGTGATAGGATCGAACTGGTACG | L |
| $A_2$(1*-2*-3*) SEQ ID NO. 18 | CCTATCACGATTAGCATTAA | achiral |
| D-$R_2$(4) SEQ ID NO. 19 | Cy3-GGCGTACCAGTTCGATCCTATC | D |
| D-$R_2$(4*-3*) SEQ ID NO. 20 | ATCGAACTGGTACGCC-BHQ2 | D |
| L-$R_2$(4) SEQ ID NO. 21 | Cy3-GGCGTACCAGTTCGATCCTATC | L |
| L-$R_2$(4*-3*) SEQ ID NO. 22 | ATCGAACTGGTACGCC-BHQ2 | L |
| D-$IN_{RNA}$ SEQ ID NO. 23 | UUAAUGCUAAUCGUGAUAGGGGU | D |

Unmodified D-oligonucleotides were purchased from IDT and all L-oligonucleotides were synthesized in house using standard solid-phase synthesis procedures. Oligonucleotides were purified by 20% denaturing polyacrylamide gel electrophoresis (PAGE; 19:1 acrylamide:bisacrylamide). Purified oligonucleotides were excised from the gel and eluted overnight at 23° C. in a buffer consisting of 200 mM NaCl, 10 mM EDTA, and 10 mM Tris (pH 7.6). The solution was then filtered to remove gel fragments, and eluted oligonucleotides were concentrated using an Amicon Ultra Centrifugal Filter (Millipore-Sigma) having a membrane pore size of 3 kDa. Following concentration, samples were desalted by ethanol precipitation.

3' labeled oligonucleotides, shown in Table 1 illustrated above, were prepared using commercial CPG resins functionalized with the corresponding modification (e.g., BHQ2) and purified as described above. Fluorescent dyes (N-hydroxysuccinimide esters) were conjugated to the 5' end of oligonucleotides via a 5' amino modification installed at the time of synthesis. Conjugation reactions were performed by combining the unpurified amino modified oligonucleotide (~20 nmol) with the appropriate dye NHS ester (5 mM final concentration) in 0.1 mL of 0.1 M sodium borate buffer (pH 8.5). Reaction mixtures were vortexed intermittently over 2 hours before being rocked gently overnight at 23° C. Samples were then passed through a NAP-5 Sephadex G-25 Column (GE Healthcare, Chicago, IL) to remove excess dye and the labeled oligonucleotide was purified by 20% denaturing PAGE as before.

Duplex reaction components for each strand-displacement reaction were assembled via a hybridization titration approach in order to achieve an ideal 1:1 ratio of the corresponding strands. Here, one strand was held constant at 5 μM while the concentration of the second strand was varied across a narrow range around 5 μM. All hybridization mixtures contained the appropriate amount of each strand, 300 mM NaCl, 1 mM EDTA, 10 mM Tris (pH 7.6), and were heated to 90° C. for 3 minutes then cooled slowly to room temperature over 1 hour. The extent of hybridization was quantified by 20% native PAGE (19:1 acrylamide:bisacrylamide) after staining with either ethidium bromide (EtBr) or, in the case of fluorescently labeled strands, fluorescence scanning with excitation/emission wavelengths at either 532 nm/560 nm (longpass filter; Cy3) or 635 nm/660 nm (longpass filter; Cy5) on a Typhoon FLA 9500 (GE Healthcare, Chicago, IL). Only those mixtures having an ideal 1:1 ratio of strands (i.e., no single-stranded oligonucleotide remained) were used further.

Each strand displacement reaction was monitored using a GloMax Discover multi-well plate reader from Promega Corp. (Madison, WI). Reactions contained 500 nM of the indicated reaction components, 300 mM NaCl, 1 mM EDTA, and 10 mM Tris (pH 7.6) and were carried out at 23° C. Reactions involving D-$IN_{RNA}$, as shown in FIG. 4, were carried out at 37° C. Reaction mixtures were prepared to a final volume of 20 μL, transferred to a 384-well microplate, and initiated by the addition of the indicated amount of input strand. The fluorescence intensity of D-reporter complexes was monitored with excitation/emission wavelengths at 520 nm/580-640 nm (bandpass filter; Cy3), while the fluorescence intensity of L-reporter complexes was monitored with excitation/emission wavelengths at 627 nm/660-720 nm bandpass filter; Cy5). All fluorescence data were normalized to a triggered reporter representing the maximum achievable signal using Equation 1, shown below.

$$F_n = \frac{F - F_0}{F_C - F_0} \qquad \text{Equation 1}$$

In Equation 1, shown above, $F_n$ is the normalized fluorescence intensity, F is the measured fluorescence, $F_0$ is the quenched fluorescence, and $F_C$ is the control fluorescence at each time a measurement was taken. This normalization equation allows accounting for the loss in signal due to photobleaching, and enables the direct comparison of the different fluorophores representing each chiral system.

In some instances, heterochiral strand-displacement reactions were analyzed by 20% native PAGE (19:1 acrylamide: bisacrylamide). Reactions were prepared as described above and incubated for 2 hours at 23° C. before an aliquot was taken (5 µL) and loaded onto a running gel. Native gels were run at 140 volts for at least 6 hours at 23° C. before being imaged as described above.

For reactions involving heteroduplex $L-A_2$, as shown in FIG. 3 and FIG. 4, a difference in the rate of strand-displacement based on the chirality of the input strand was observed. The rate constant for each of these strand-displacement reactions were determined. Briefly, reaction mixtures containing 500 nM $L-A_2$, 1.5 µM $L-R_2$, 300 mM NaCl, 1 mM EDTA, and 10 mM Tris (pH 7.6) were initiated by the addition of 750 nM of the appropriate input strand and the progress of the reactions was monitored by spectrofluorimetry. Under these conditions, the reporter kinetics did not limit the reaction rate. The reactions were performed with 1.5 equivalent of the input strand relative to $L-A_2$ in order to ensure complete invasion of the heteroduplex substrate.

The fluorescence data was fit using an equation derived from the second-order rate law with respect to the input strand and heteroduplex $L-A_2$. Due to the stability of the waste strands, reverse reactions were considered negligible. The rate constants for the strand-displacement reactions were extracted using a second-order rate model to be $2.14 \times 10^4$ $M^{-1}$ $s^{-1}$, $9.56 \times 10^2$ $M^{-1}$ $s^{-1}$, and $5.13 \times 10^3$ $M^{-1}$ $s^{-1}$ for $L-IN_2$, $D-IN_2$, and $D-IN_{RNA}$, respectively, as indicated in FIG. 5.

Figure 1B:
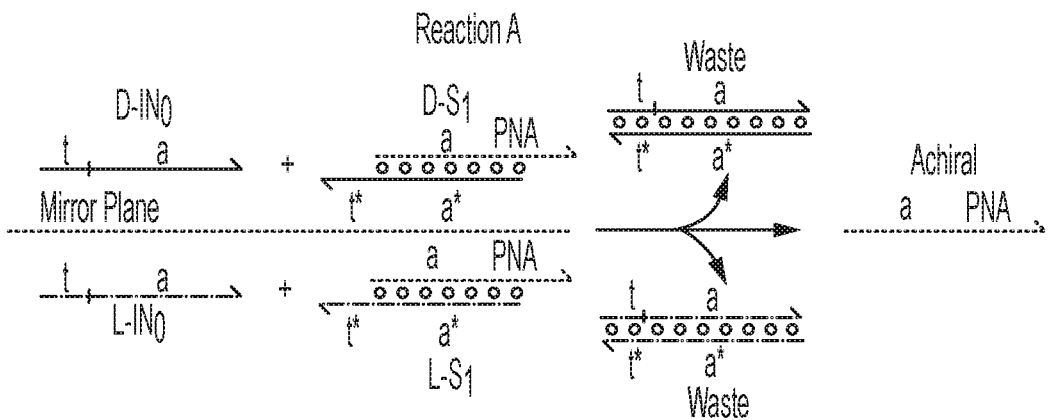
FIG. 1B and FIG. 1C illustrate mechanisms for heterochiral strand-displacement reactions A (FIG. 1B) and B (FIG. 1C). DNA and PNA strands are depicted as lines with the half arrow denoting the 3' end (or C-terminus for PNA), and an asterisk indicating complementarity.
Figure 1C:
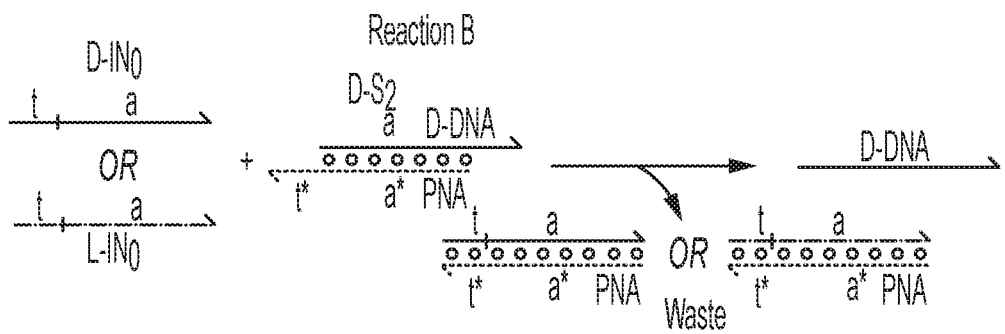

PNA, illustrated in FIG. 1A, is an oligonucleotide analog in which the sugar-phosphate backbone has been replaced with uncharged N-(2-aminoethyl)glycine units. Like DNA and RNA, PNA obeys WC base pairing rules, forming stable antiparallel duplexes with DNA. In contrast to the native polymers, however, PNA has no inherent chirality, and as a result, hybridizes to DNA or RNA irrespective of chirality. On the basis of this property, two toehold-mediated strand-displacement reactions (hereinafter strand-displacement reactions) that exploit DNA/PNA heteroduplexes in order to interface the two enantiomers of DNA, as shown in FIG. 1B and FIG. 1C, were conceived. In Reaction A, shown in FIG. 1B, a DNA/PNA substrate complex ($S_1$) is activated via binding of a DNA input ($IN_0$) to its DNA toehold domain (t*), resulting in displacement of the achiral PNA strand. In this reaction, the chirality of input signal matches the chirality of the incumbent DNA strand on the DNA/PNA heteroduplex. Release of the PNA strand effectively decouples the stereochemical information from the sequence information present in the chiral input. At this point, the achiral PNA output can serve as a sequence-specific input for downstream reactions with either D-DNA or L-DNA components. In Reaction B, shown in FIG. 1C, the toehold domain (t*) resides on the achiral PNA strand in the initial DNA/PNA substrate complex (S). Therefore, $S_2$ can be activated by either D-DNA or L-DNA inputs ($D-IN_0$ or $L-IN_0$, respectively) to directly generate an output having a single, predetermined chirality.

Using Reaction A as a starting point for developing a heterochiral DNA nanodevice, a multilayer DNA strand-displacement circuit was designed employing both enantiomers of each reaction component, as illustrated in FIG. 2A. The input strand (e.g., $D-IN_1$) reacts with the chimeric DNA/PNA complex (e.g., $D-A_1$) via toehold domain (1), resulting in displacement of the achiral PNA intermediate ($PNA_1$). The activated domain (2*) on the PNA serves as the input for a second reaction with complex $B_1$ (e.g., $D-B_1$), releasing the output strand (e.g., $D-OUT_1$). Depending on the chirality of the DNA components provided, the circuit can proceed through several possible reaction pathways, as illustrated in FIG. 2C. For example, a circuit comprised solely of components $D-A_1$ and $D-B_1$ can only generate $D-OUT_1$ in the presence of $D-IN_1$ (pathway P1). This is analogous to the traditional, homochiral approach (i.e., if the achiral PNA were to be replaced with a D-DNA strand having the same sequence). However, addition of $L-B_1$ to the same reaction mixture enables simultaneous production of both enantiomers of $OUT_1$ (pathway P3, shown in FIG. 2C), each of which can carry out unique downstream functions.

To confirm the above design, pathways P2 and P5 were examined in isolation, as illustrated in FIG. 2C, both of which produce a DNA output having the opposite chirality as the input. In order to stereospecifically monitor the outputs of the circuit, a pair of chiral reporter complexes ($D-R_1$ and $L-R_1$) having unique fluorophore-quencher pairs (Cy3/BHQ2 and Cy5/BHQ3, respectively) were utilized, as illustrated in FIG. 2B. As shown in FIG. 2D, when $D-IN_1$ was added to a reaction mixture containing only pathway P2 components ($D-A_1$ and $L-B_1$), along with both reporter complexes, only the fluorescent signal corresponding to activation of $L-R_1$ (Cy5) was observed. Likewise, only reporter $D-R_1$ (Cy3) was activated when $L-IN_1$ was added to a reaction mixture containing solely pathway P5 components ($L-A_1$ and $D-B_1$). In contrast, no significant fluorescent signal was observed for either reaction in the absence of an input or in the presence of an input with the opposite (orthogonal) chirality relative to complex $A_1$. These fluorescent data were further verified by gel electrophoresis. Together, these results confirm that pathways P2 and P5 of the heterochiral circuit function as intended, and demonstrate for the first time an autonomous heterochiral DNA device.

Figure 7:
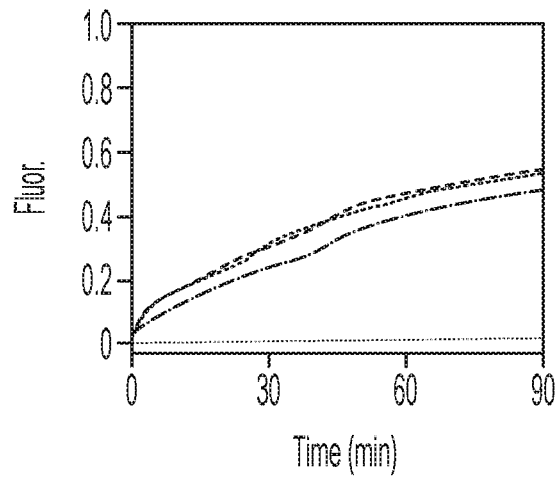
FIG. 7 illustrates confirmation of output (OUT$_1$) orthogonality for the heterochiral circuit depicted in FIG. 2A (pathway P3). Strand-displacement reactions were carried out as described with respect to FIG. 2D (pathway P3), however, reporter complex D-R$_1$ was either omitted (short-dash or dotted lines) or present in 2-fold excess relative to L-R$_1$ (long-dash or dot-dash lines). The fluorescent signals were generated via activation of either reporter complex D-R$_1$ (Cy3), shown by dot-dash and dotted lines or L-R$_1$ (Cy5) shown by long-dash and short-dash lines.

Having demonstrated the proper function of pathways P2 and P5 in isolation, their corresponding components were combined into a single reaction mixture in order to construct the complete heterochiral circuit depicted in FIG. 2A. All reaction components ($D-A_1$, $L-A_1$, $D-B_1$, and $L-B_1$), as well as both reporter complexes ($D-R_1$ and $L-R_1$), were present at equimolar concentrations (500 nM). Addition of one equivalent of $D-IN_1$ (500 nM) to the racemic circuit resulted in generation of approximately half the maximal fluorescent signal for each reporter complex, illustrated in FIG. 2D, pathway P3, suggesting that ~0.5 equivalent (~250 nM) of each output strand was produced relative to the input. This observation is consistent with the equal consumption of the achiral PNA strand ($PNA_1$) by each enantiomer of complex $B_1$ (pathway P3). Accordingly, doubling the concentration of the input ($D-IN_1$), as well as both $D-A_1$ and $L-A_1$ complexes, resulted in near stoichiometric activation of both chiral reporters, as shown in FIG. 2D. As anticipated, similar results were obtained using $L-IN_1$ in place of $D-IN_1$, as illustrated in FIG. 6, pathway P6. The fluorescent signal associated with $L-R_1$ (Cy5) remained unaffected when the reaction (pathway P3) was carried out in the absence of reporter D-R$_1$ or in the presence of a 2-fold excess of D-R$_1$ relative to L-R$_1$, illustrated in FIG. 7, which further confirms absolute orthogonality between D-OUT$_1$ and L-OUT$_1$ (and D-DNA and L-DNA in general). Due to its ability to convert an enantiomerically pure DNA input into a 1:1 mixture of orthogonal D-DNA and L-DNA outputs, this circuit is termed a "racemization gate", the outputs of which offer a general route to parallelization of DNA circuitry or other dynamic DNA devices without a concomitant increase in crosstalk between reaction components.

In order to demonstrate the application of Reaction B of FIG. 1C in a DNA circuit, a simple "chirality OR" gate was constructed capable of generating an L-DNA output (L-OUT$_2$) from either a D-DNA (D-IN$_2$) or a L-DNA (L-IN$_2$) input having the identical sequence, illustrated in FIG. 3A. Thus, the chirality of the input rather than its sequence represents logic values, as illustrated in FIG. 3B and Table 2, shown below. Again, a stereospecific reporter complex (L-R$_2$) was exploited in order to monitor the progress of the reaction. As shown in FIG. 3B, the experimental data exhibited the expected Boolean OR logic; the presence of either D-IN$_2$ or L-IN$_2$ ({1,0} and {0,1}, respectively) gave rise to a fluorescent signal that was at least 20-fold stronger than the maximum response seen in the absence of an input ({0,0}). These data were further verified by gel electrophoresis. This is the first example of a chirality-based DNA computation.

TABLE 2

| Inputs | | Output |
| --- | --- | --- |
| D-IN$_2$ | L-IN$_2$ | y |
| 0 | 0 | 0 |
| 0 | 1 | 1 |
| 1 | 0 | 1 |
| 1 | 1 | 1 |

Figure 8:
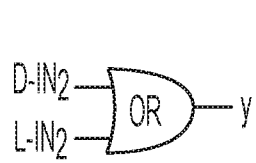
FIG. 8 illustrates a demonstration of the heterochiral OR gate (FIG. 3A) using heteroduplex D-A$_2$ and reporter complex D-R$_2$ in place of their corresponding L-versions. Reactions were carried out as described with respect to FIG. 3B.
Figure 8:
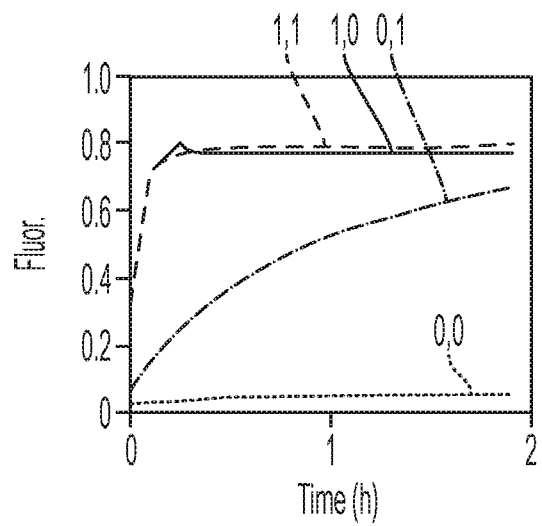

The data revealed that the chirality OR gate functioned significantly slower with D-IN$_2$ ((1,01) than with either input containing L-IN$_2$ ({0,1} and {1,1}), illustrated in FIG. 3B and Table 2, shown above. This observation is likely attributed to DNA strand L-OUT$_2$ inducing a left-handed chirality onto the complexed PNA strand (i.e., heteroduplex L-A$_2$ is a left-handed helix). Therefore, the strand-displacement reaction between L-A$_2$ and D-IN$_2$ (but not L-IN$_2$) is expected to incur an energetic penalty due to the inversion of duplex helicity en route to product formation, reducing the overall reaction rate. Consistent with this explanation, when inverting the configuration of complex A$_2$ and replacing L-A$_2$ with D-A$_2$ (a right-handed helix), the opposite trend in reactivity was observed, illustrated in FIG. 8.

The enantioselectivity of Reaction B represents a potential chirality-based strategy for engineering control over the kinetics of DNA strand-displacement devices, which is typically achieved by varying toehold length. To this end, a "chirality threshold" gate was built by combining both enantiomers of the A$_2$ heteroduplex, along with their corresponding reporter complexes, into a single reaction mixture, illustrated in FIG. 3C. Here, the input signal (D-IN$_2$) reacts much faster with D-A$_2$ (i.e., the threshold) than with L-A$_2$ because the toehold-mediated strand-displacement rate is dependent on chirality. Therefore, the desired output (L-OUT$_2$) can be produced in a significant amount once the input signal (D-IN$_2$) exceeds the threshold component (D-A$_2$). Both thresholding (D-OUT$_2$) and production of the output signal (L-OUT$_2$) were monitored simultaneously using reporters D-R$_2$ (Cy3) and L-R$_2$ (Cy5), respectively, illustrated in FIG. 3D and FIG. 3E.

When the input signal (D-IN$_2$) was in excess, relative to the threshold component (D-A$_2$), significant output signal produced (L-OUT$_2$), illustrated in FIG. 3F, thereby confirming desirable thresholding behavior. The broader significance of these data is the demonstration that the heterochiral circuit can be used to time the release of two orthogonal output signals, for example, D-OUT$_2$ and L-OUT$_2$, based on the amount of input provided. The circuit, in effect, represents a kinetically controlled version of the DNA racemization gate.

The ability of Reaction B, of FIG. 1C, to translate a natural D-RNA input signal into an L-DNA output signal, providing a strategy to autonomously interface endogenous nucleic acids with diagnostic and/or therapeutic nanodevices comprised of bioorthogonal L-DNA was investigated.

The input strand (D-IN$_2$) is the DNA analog of microRNA-155, an oncogenic microRNA implicated in cancer development—the heterochiral strand-displacement reaction depicted in FIG. 3A was designed with this application in mind. Accordingly, when this circuit was initiated with microRNA-155 (D-IN$_{RNA}$), illustrated in FIG. 4A, it behaved in the same manner, rapidly generating a fluorescent signal corresponding to production of L-OUT$_2$, illustrated in FIG. 4B. In fact, the reaction occurred faster with the RNA input (D-IN$_{RNA}$, 5.13×10$^3$ M$^{-1}$ s$^{-1}$) than with the DNA input (D-IN$_2$, 9.56×10$^2$ M$^{-1}$ s$^{-1}$), illustrated in FIG. 5. The circuit also behaved properly in the presence of excess nonspecific RNA (HeLa cell nuclear RNA), demonstrating the specificity of the heterochiral strand-displacement reaction. All reactions were carried out at 37° C. Taken together, these data indicate that heterochiral circuitry is compatible with biologically relevant D-RNA inputs, providing a starting point for engineering bioorthogonal L-DNA-based nanodevices that interact with and operate within living cells.

In summary, presented in detail above are designs and implementations of two strand-displacement reactions capable of interfacing the two orthogonal enantiomers of DNA in a sequence-specific manner, as illustrated in FIG. 1, thereby establishing chirality as a design parameter for DNA nanotechnology. Because these heterochiral strand-displacement reactions adhere to simple WC base pairing rules, they can be easily integrated with the majority of preexisting homochiral systems. This provides an opportunity not only to parallelize traditional strand-displacement circuitry, but also to increase the varieties of architectures and dynamic behaviors that can be programed into DNA-based nanodevices. In addition, the recent discovery of "cross-chiral" aptamers and ribozymes, both of which interact with nucleic acids of opposing chirality through shape rather than sequence complementarity, may expand the toolkit for engineering heterochiral DNA nanotechnology.

L-DNA is resistant to both nuclease degradation and off-target interactions with native nucleic acids and proteins. Thus, the demonstration of sequence-specific interfacing of a biologically relevant RNA species (microRNA) with L-DNA lays the foundation for integrating endogenous nucleic acid signals with L-DNA-based "biocomputers" capable of performing autonomous diagnostic and therapeutic tasks in living organisms free of obstruction from cellular components. This can remove a significant source of design constraints in the burgeoning field of in vivo DNA nanotechnology. Towards this goal, the heterochiral circuit depicted in FIG. 4A could be employed as a bioorthogonal sensor for oncogenic microRNA-155.

MiRNAs are a large family of short, non-coding RNAs that play a role in post-transcriptional regulation of gene expression. Moreover, aberrant miRNA expression is associated with a wide range of human diseases, including, but not limited to, cancer. Consequently, significant efforts have been made to image miRNA expression in living cells and organisms, which not only provides unparalleled insight into the biological functions and dynamics of these important molecules, but also holds great promise for early disease detection. Owing to the straightforward programmability of WC base-pairing rules, current strategies for imaging endogenous miRNAs mostly rely on the use of hybridization-based probes, such as molecular beacons, binary probes, and molecular switches, all of which are comprised of nucleic acids. Despite their success for imaging miRNA in living cells, nucleic acid based-probes still suffer from two key limitations when applied to biological environments: rapid nuclease degradation and unintended interactions with endogenous macromolecules, both of which adversely affect performance and/or sensitivity of the probe. Thus, development of biocompatible nucleic acid-based probes for live-cell miRNA imaging remains an unmet need.

In principle, many of the disadvantages associated with the use of nucleic acids in live cells can be overcome by simply inverting the stereochemistry of the sugar backbone. L-(deoxy)ribose-based nucleic acids (L-DNA and L-RNA), which are synthetic enantiomers of natural D-nucleotides, are intrinsically resistant to nuclease degradation and less susceptible to off-target interactions with cellular components. Therefore, L-nucleic acid-based molecular probes are expected to have dramatically improved intracellular performance, reliability, and utility compared to those comprised of the native stereoisomer. Despite these advantages, however, L-oligonucleotides are incapable of forming contiguous WC base pairs with native D-nucleic acids, which until now has limited their usefulness in the design of hybridization-based probes for imaging endogenous RNAs.

In order to overcome this limitation, strand-displacement methodology for sequence-specifically interfacing oligonucleotides of opposite stereochemistry can be utilized. The approaches presented herein take advantage of PNA, which unlike native oligonucleotides, has no inherent chirality. As a result, PNA hybridizes to both DNA and RNA irrespective of stereochemistry. On the basis of this property, PNA can serve as an intermediary allowing D-oligonucleotides and L-oligonucleotides to be interfaced in a sequence-specific manner. Using this approach, the imaging of RNA in live cells using a programmable, hybridization-based sensor comprised of bio-orthogonal L-nucleic acids is discussed in further detail below.

Oligonucleotides were either purchased from Integrated DNA Technologies (Coralville, IA) or prepared by solid-phase synthesis on an Expedite 8909 DNA/RNA synthesizer. DNA synthesis reagents and CPG residues were purchased from Glen Research (Sterling, VA), and L-nucleoside phosphoramidites were purchased from ChemGenes (Wilmington, MA). Peptide nucleic acids (PNAs) were purchased from PNA Bio, Inc. (Newbury Park, CA) at 99.9% purity and were not purified further. The thiazole orange (TO) dye used in the present disclosure, which is often referred to as TO1-Biotin, and was purchased from Applied Biological Materials Inc. (Richmond, BC).

L-RNAs were synthesized in house using standard solid-phase synthesis procedures and purified by 20% denaturing polyacrylamide gel electrophoresis (PAGE; 19:1 acrylamide:bisacrylamide). D-RNA variants of the Mango III aptamer (M-0-M-4, shown in FIG. 9) were prepared by run-off transcription of the corresponding DNA templates, which were generated by cross-extension of two overlapping synthetic oligonucleotides, illustrated in Table 3, shown below. Briefly, oligonucleotides (200 pmol each) where annealed in a 25 µL mixture containing 6 mM $MgCl_2$, 150 mM KCl, 20 mM DTT, and 100 mM Tris (pH 8.3), which was heated at 90° C. for 1 minute and then cooled slowly to 22° C. The volume was then adjusted to 50 µL using a solution containing 1.0 mM of each of the four dNTPs and 16 U/µL Reverse Transcriptase and incubated at 42° C. for 45 minutes. Following ethanol precipitation, the resulting dsDNA was added to a transcription reaction mixture containing 10 U/µL T7 RNA polymerase, 0.001 U/µL Inorganic pyrophosphatase (IPP), 25 mM $MgCl_2$, 2 mM spermidine, 10 mM DTT, 40 mM Tris (pH 7.9), and 5 mM of each of the four NTPs. After incubating for 2.5 h at 37° C., reaction mixture was ethanol precipitated and the RNA purified by denaturing PAGE (10%, 19:1 acrylamide:bis-acrylamide). Purified oligonucleotides were excised from the gel and eluted overnight at 23° C. in a buffer consisting of 200 mM NaCl, 10 mM EDTA, and 10 mM Tris (pH 7.6). The solution was then filtered to remove gel fragments, and eluted oligonucleotides were concentrated using an Amicon Ultra Centrifugal Filter (MilliporeSigma, Burlington, MA) having a membrane pore size of 3 kDa. Following concentration, all samples were desalted by ethanol precipitation. Table 3, shown below, illustrates oligonucleotides used to prepare DNA templates for in vitro transcription of D-M-0-4.

TABLE 3

| Product RNA | Synthetic Oligonucleotides Used for Template Assembly (5' → 3') |
| --- | --- |
| D-M-0<br>SEQ ID NO. 24 | TAATACGACTCACTATAGGGGCACGTACGAAGGAA<br>GGATTGGTAGGCACGTACGAATATACCACATACCA<br>ATCCTTCCTTCG |
| D-M-1<br>SEQ ID NO. 25 | TAATACGACTCACTATAGGAATCGTGATAGGCGAA<br>GGAAGGATTGATAGGCGAATATACCACATACCAAT<br>CCTTCCTTCGCCTA |
| D-M-2<br>SEQ ID NO. 26 | TAATACGACTCACTATAGGAATCGTGATAGGGGAA<br>GGATTGATAGGCGAATATACCACATACCAATCCTT<br>CCCCTA |
| D-M-3<br>SEQ ID NO. 27 | TAATACGACTCACTATAGGAATCGTGATAGGCGAA<br>GGAAGGATTGGCGAATATACCACATACCAATCCTT<br>CCTTCGCCTA |
| D-M-4<br>SEQ ID NO. 28 | TAATACGACTCACTATAGGTAATCGTGATAGGAAG<br>GATTCGTGATATATACCACATACCAATCCTTCCTA<br>TCACGA |

Each D-RNA Mango III variant (M-1-M-4; 10 µM) was annealed to the PNA blocking strand (P1; 10 µM) in a reaction mixture containing 1 mM EDTA (pH 7). The reaction was heated at 90° C. for 1 minute before being slowly cooled to room temperature. Both the blocked (pM-1-M-4) and unblocked (M-1-M-4) version of each Mango III variant were diluted to 400 nM in separate reaction mixtures containing 400 nM TO, 100 mM KCl, 0.5 mM $MgCl_2$, and 10 mM HEPES (pH 7.4) and were incubated at 37° C. for 10 minutes. The fluorescence intensity of each reaction mixture was monitored using a GloMax Discover multi-well plate reader from Promega Corp. (Madison, WI) with excitation/emission wavelengths at 475 nm/500-550 nm (bandpass filter for GFP).

Figure 10A:
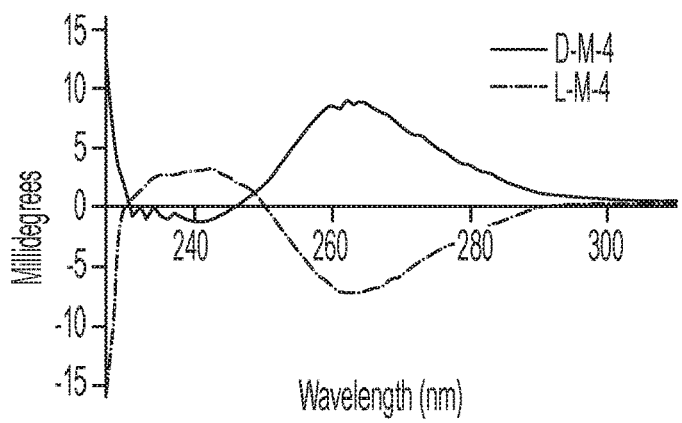
FIG. 10A illustrates CD spectra of D-M-4 and L-M-4 in the presence of a buffer containing 100 mM KCl, 0.5 mM MgCl$_2$, and 10 mM HEPES (pH 7.4).

For CD experiments, illustrated in FIG. 10A, D-M-4 and L-M-4 (5 RM) were folded as described above in a buffer containing 100 mM KCl, 0.5 mM $MgCl_2$, and 10 mM HEPES (pH 7.4). Data were obtained from a 450 µL sample in a quartz cuvette using an Applied Photophysics Chirascan spectrophotometer (Leatherhead, England) at 1 nm intervals from 220 to 310 nm. All data were collected at a constant temperature of 37° C.

-M-4 or L-M-4 aptamers (1 µM) were added to separate reaction mixtures containing 10% FBS, 100 mM KCl, 0.5 mM $MgCl_2$, and 10 mM HEPES (pH 7.4). An aliquot was taken from each reaction mixture at the indicated times and quenched in a solution containing 90% formamide in 10 mM EDTA. Samples were then analyzed by 20% denaturing PAGE (19:1 acrylamide:bisacrylamide).

Detection of miRNA-155 in solution, illustrated in FIG. 11 was carried out using the indicated stereoisomer (D or L) of either M-4 or pM-4 (400 nM), 0% or 10% FBS, 0 or 400 nM D-IN, 400 nM TO, 100 mM KCl, 0.5 mM $MgCl_2$, and 10 mM HEPES (pH 7.4) at 37° C. Reaction mixtures were prepared to a final volume of 50 µL and the fluorescence intensity was monitored as a function of time using a GloMax Discover multi-well plate reader from Promega Corp. (Madison, WI) with excitation/emission wavelengths at 475 nm/500-550 nm (bandpass filter for GFP). In order to avoid degradation of the miR-155 input (D-IN) prior to sensor activation, a DNA version of D-IN was used when 10% FBS was included in the reaction mixture. All other reaction conditions remained the same.

Proper assembly of the pM-4 sensor and subsequent strand-displacement by D-IN was also confirmed by 20% native PAGE (19:1 acrylamide:bisacrylamide). Reaction mixtures were prepared as described above and incubated for 2 hours at 37° C. before an aliquot was taken (5 µL) and loaded onto the running gel. Native gels were run at 100 volts for at least 6 hours at 23° C. The gel was stained with ethidium bromide (EtBr) and imaged on a Typhoon FLA 9500 (GE Healthcare, Chicago, IL).

Wild-type HeLa cells were obtained from ATCC (Manassas, VA) and cultured in Dulbecco's Modified Eagle's Medium (DMEM; Thermo Fisher Scientific) supplemented with 10 mM HEPES, 1 mM GlutaMax, 100 U/mL penicillin-streptomycin and 10% FBS. Stably transfected HeLa cell lines were cultured similarly with addition of puromycin at 10 µg/ml. All cells were maintained at 37° C. in a humidified $CO_2$ (5%) atmosphere.

An ~300 bp fragment of the microRNA-155 gene (centered around the mature miRNA-155 sequence) was amplified from human genomic DNA using primers 155-Fwd and 155-Rev, shown in Table 4 below, and inserted between the BamHI and NheI restriction site within the pEGP-miR plasmid (Cell Biolabs Inc., San Diego, CA). The eGFP gene present in the pEGP-miR plasmid backbone was deleted using the Phusion Site-Directed Mutagenesis Kit (Thermo Fisher Scientific) employing primers GFP-Fwd and GFP-Rev, illustrated in Table 4 below, to give the final miRNA-155 expression plasmid (pEGP-155). A similar plasmid lacking the miR-155 DNA fragment was also constructed as a control (pEGP-Null). Correct assembly of both plasmids was confirmed by DNA sequencing (Eton Bioscience Inc., San Diego, CA). Table 4, shown below, illustrates names and sequences of oligonucleotides used according to an aspect of the present disclosure.

TABLE 4

| Sequence Name | Sequence Identity 5' → 3' |
|---|---|
| D-M-0<br>SEQ ID NO. 29 | GGCACGUACGAAGGAAGGAUUGGUA<br>UGUGGUAUAUUCGUACGUGCC |
| D-M-1<br>SEQ ID NO. 30 | GGAAUCGUGAUAGGCGAAGGAAGGA<br>UUGGUAUGUGGUAUAUUCGCCUAUC |
| D-M-2<br>SEQ ID NO. 31 | GGAAUCGUGAUAGGAAGGAAGGAUU<br>GGUAUGUGGUAUAUUCCUA |
| D-M-3<br>SEQ ID NO. 32 | GGAAUCGUGAUAGGCGAAGGAAGGA<br>UUGGUAUGUGGUAUAUUCGCC |
| D-M-4<br>SEQ ID NO. 33 | GGUAAUCGUGAUAGGAAGGAUUGGU<br>AUGUGGUAUAUAUCACG |
| P1<br>SEQ ID NO. 34 | CTATCACGATTAGCATTAA |
| L-M-4<br>SEQ ID NO. 35 | UAAUCGUGAUAGGAAGGAUUGGUAU<br>GUGGUAUAUAUCACG |
| L-M-4.chol<br>SEQ ID NO. 36 | TGGATATCTAGAATGTACGTACGGT/<br>Spacer18/UAAUCGUGAUAGGAAGG<br>AUUGGUAUGUGGUAUAUAUCACG |
| Chol<br>SEQ ID NO. 37 | ACCGTACGTACATTCTAGATATCCA/<br>Cy5/Cholesterol-TEG/ |
| D-IN<br>SEQ ID NO. 38 | UUGGGGAUAGUGCUAAUCGUAAUU |
| 155-Fwd<br>SEQ ID NO. 39 | TCGAGGATCCTCTCTCTTGCAGGTG<br>GCACAAACC |
| 155-Rev<br>SEQ ID NO. 40 | TCGAGCTAGCAGTCTAAGTTTATCC<br>AGCAGGG |
| GFP-Fwd<br>SEQ ID NO. 41 | /5Phos/GCCACCATGACCGAGTAC |
| GFP-Rev<br>SEQ ID NO. 42 | /5Phos/GGTGTGTCAGAATTCAGA<br>TCTC |

Figure 12:
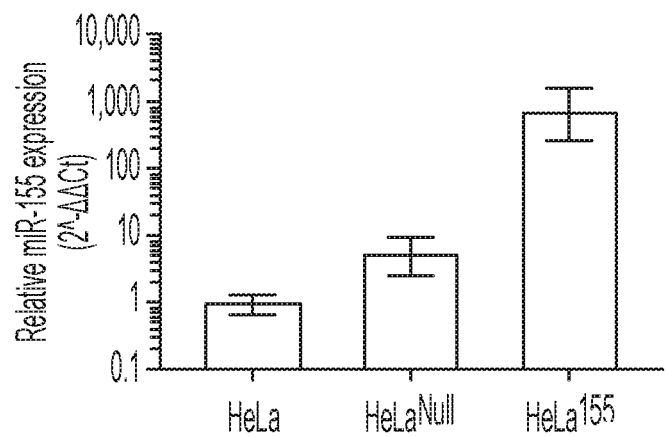
FIG. 12 shows relative expression levels of miR-155 in different HeLa cell lines as determined by qRT-PCR ($2^{-\Delta\Delta Ct}$ method).

HeLa cells were transfected with either pEGP-155 ($HeLa^{155}$) or pEGP-Null ($HeLa^{Null}$) using FuGene HD (Promega Corp., Madison, WI) according to the manufacturer's protocol. Transfected cells were selected under 10 µg/ml puromycin for at least 2 weeks. Cells that survived the initial selection were diluted to proximately one cell/well is a 96-well dish and selected for an additional 2 weeks in order to obtain clonal purity. Expression level of miRNA-155 was determined by qRT-PCR, discussed in further detail below, and illustrated in FIG. 12.

Total RNA from both wild-type and stably-transfected HeLa cells was extracted using Quick-RNA MiniPrep Kit (Zymo Research, Irvine, CA). Small RNAs (<200 nt) were fractionated according to the manufacturer and reverse-transcribed using the TaqMan Advanced miRNA cDNA Synthesis Kit (Thermo Fisher Scientific, Waltham, MA). Three separate reverse-transcription reactions were carried out for each extracted RNA sample. The qRT-PCR analysis was performed on each sample using TaqMan Advanced miRNA Assays for hsa-mir-155-5p and hsa-mir-191-5p on a CFX96 qRT-PCR system (Bio-Rad Laboratories, Hercules, CA). Data was evaluated with respect to miRNA-155 expression by normalizing to the expression of miRNA-191 using the $2^{-\Delta\Delta Ct}$ method.

In order to visualize cellular uptake of the sensor, wild-type HeLa cells were plated onto a 96-well dish at $10^5$ cells/ml in DMEM. On the following day, the culture media was replaced with Opti-MEM (supplemented with 2.5% FBS) and the cells were treated with 100 nM each L-M-4.chol and TO. After the indicated incubation times, the cells were washed with PBS buffer and the media was replaced with FluoroBrite DMEM (Thermo Fisher Scientific, Waltham, MA). Fluorescence was imaged with an EVOS FL Auto 2 Cell Imaging System (Thermo Fisher Scientific, Waltham, MA) using Mango (YFP; ex, BP500/24; em, BP524/27) and Cy5 (ex, BP628/40; em, 692/40) light cubes at 40× magnification.

In order to image miRNA-155 expression in living cells, wild-type HeLa, HeLa$^{155}$, and HeLa$^{Null}$ cells were plated onto a 96-well dish at $10^5$ cells/ml in DMEM. On the day of experiment, the culture media was replaced with Opti-MEM (supplemented with 2.5% FBS) and cells were treated with 100 nM TO and 100 nM of either L-M-4.chol or L-pM-4.chol. After 12 hours, the media was replaced with FluoroBrite DMEM (Thermo Fisher Scientific) and fluorescence was imaged with an EVOS FL Auto 2 Cell Imaging System (Thermo Fisher Scientific) using Mango (YFP; ex, BP500/24; em, BP524/27) and Cy5 (ex, BP628/40; em, BP692/40) light cubes at 10× magnification.

All images were processed using Celleste Image Analysis Software (Thermo Fisher Scientific, Waltham, MA) and ratiometric quantification of fluorescence data was carried out using the Equation 2, shown below.

$$\text{Ratio}_{mango/cy5} = \frac{(F_{mango} - F^0_{mango})}{(F_{cy5} - F^0_{cy5})} \quad \text{Equation 2}$$

In Equation 2, shown above, $F_{mango}$ and $F_{cy5}$ are the average fluorescence intensities for Mango and Cy5, respectively, and $F_{mango}^0$ and $F_{cy5}^0$ are the average fluorescence intensities caused by the black background within the same image. Data was averaged from at least six images from two separate experiments.

Cells were plated onto a 96-well dish at $10^5$ cells/ml in DMEM and incubated for 12 hours as described above. Cells were then trypsinized, pelleted by centrifugation, and resuspended in 200 µL Opti-MEM. Fluorescence data was collected using an Accuri C6 Flow Cytometer (BD Biosciences, San Jose, CA). The Mango fluorescence signal was quantified using FL-1 (ex, 488; em, BP533/30) and the Cy5 fluorescence signal was quantified using FL-4 (ex, 640; em, BP675/25) and data was further processed using FlowJo software (FlowJo, LLC).

Figure 9A:
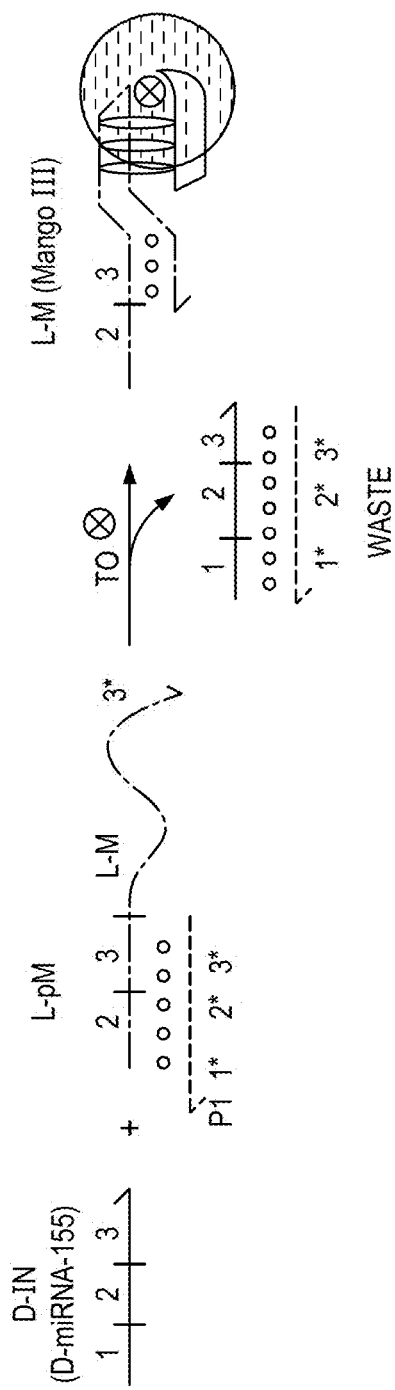
FIG. 9A shows a schematic illustration of the heterochiral strand-displacement sensor mechanism. Oligonucleotides are depicted as lines with the half arrow denoting the 3' end (or C-terminus for PNA), and an asterisk indicating complementarity. D-DNA (solid line), L-DNA (dot-dash line), and PNA (dotted line).

As depicted in FIG. 9A, the sensor (L-pM) includes a heteroduplex between an achiral PNA strand (P1) and a fluorogenic aptamer comprised of L-RNA (L-M). Fluorogenic aptamers are engineered to bind non-fluorescent small molecule dyes, resulting in strong fluorescent activation. In the present disclosure, the recently identified Mango III aptamer were chosen as the model system due to its bright fluorescent signal, high binding affinity towards its target dye (thiazole orange; TO), and small size relative to other fluorogenic aptamers (e.g., Spinach and Broccoli). Importantly, TO dyes are achiral, implying that they can be bound and activated by both D-versions and L-versions of Mango III. In the absence of the D-RNA input (D-IN), folding of a critical stem domain (3/3*) in the aptamer is blocked by the bound PNA strand, illustrated in FIG. 9A. Because the toehold domain (1*) resides on the achiral PNA, D-IN can still bind to the sensor (via 1 and 1*) and displace the incumbent L-Mango III aptamer (L-M) from the PNA blocking strand. This enables proper folding of the aptamer, which in turn activates an enhanced fluorescent signal by binding TO.

Figure 9B:
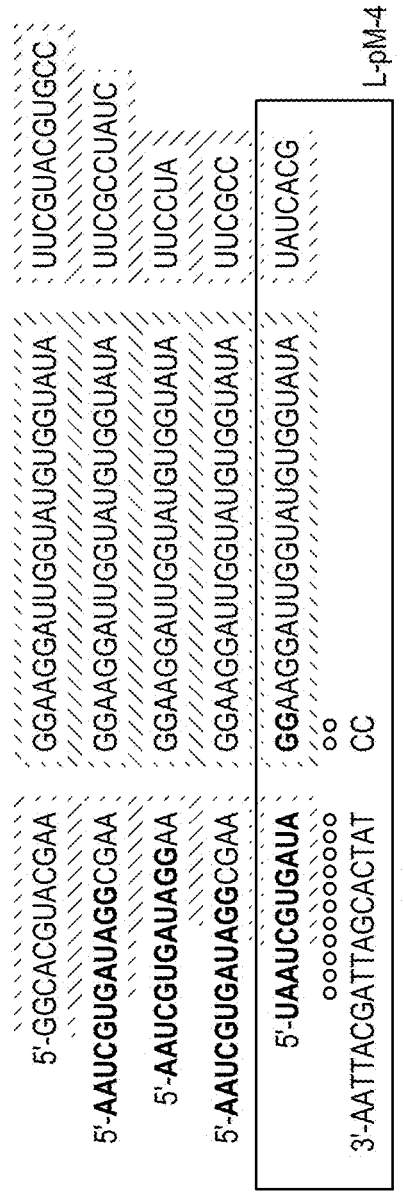
FIG. 9B shows sequences of oligonucleotides according to an aspect of the present disclosure. The core TO binding domain of the Mango III aptamer is shaded in forward slash-dashed lines and the closing stem domain (3/3*) is shaded in backward slash-dashed lines. The PNA binding site for each Mango III variant (M-1-4) is indicated by bold lettering.
Figure 9C:
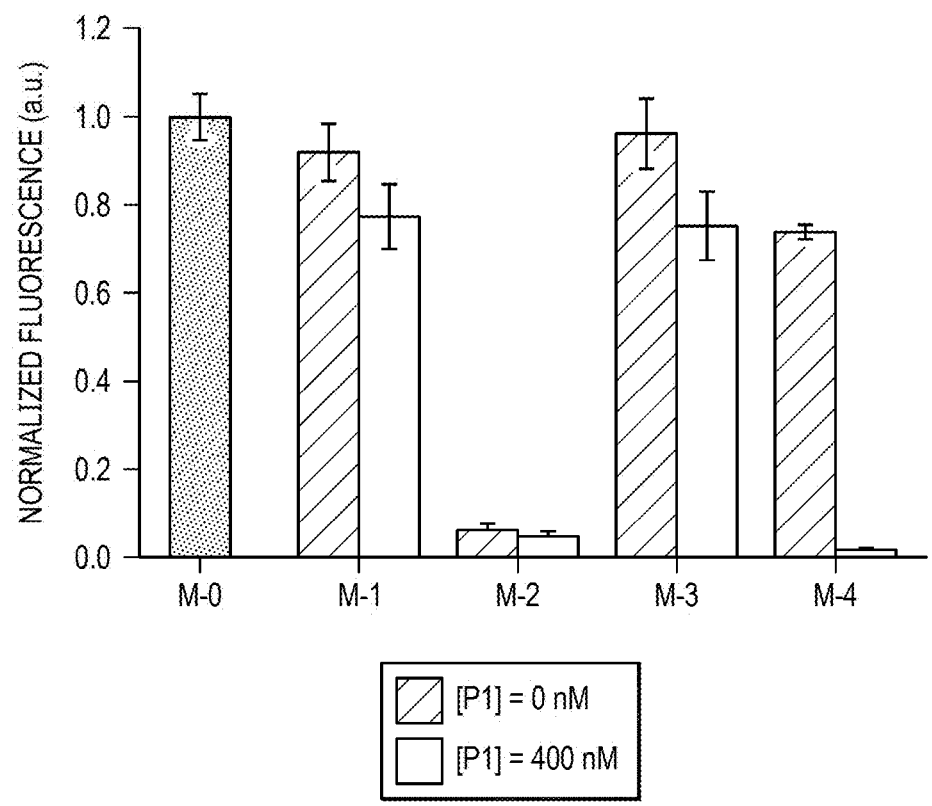
FIG. 9C illustrates optimization of the signal-to-background ratio based on different sequence designs. Reactions contained either 0 or 400 nM P1, 400 nM of the indicated aptamer, 400 nM TO dye, 100 mM KCl, 0.5 mM MgCl$_2$, and 10 mM HEPES (pH 7.4) and were carried out at 37° C. for 10 min. Fluorescence values were normalized to wild-type Mango III (M-0).

The sensor was designed based on the sequence of the PNA blocking strand (P1), which was itself complementary to the intended intracellular target, miRNA-155, D-IN, illustrated in FIG. 9B. MiRNA-155 is a prototypical oncogenic miRNA associated with the development and invasiveness of various types of malignancies. Based on the sequence of miRNA-155, the sequence of the closing stem domain of Mango III (3/3*) required significant changes compared to the parent aptamer, M-0, illustrated in FIG. 9B. However, biochemical and structural studies indicated that the sequence of this stem can be varied, as long as complementarity is maintained. Based on this design consideration, several D-RNA versions of the Mango III aptamer (M-1-4) were prepared, varying the length of domains 2 and 3, as well as the position of the PNA binding site relative to the 5' end of the aptamer. The ability of the PNA strand (P1) to prevent folding of the aptamer in the presence of TO, illustrated in FIG. 9C, was examined. Based on this examination, it was found that D-M-4 exhibited good signal-to-background ratio in the presence of the PNA (>70-fold).

Figure 10B:
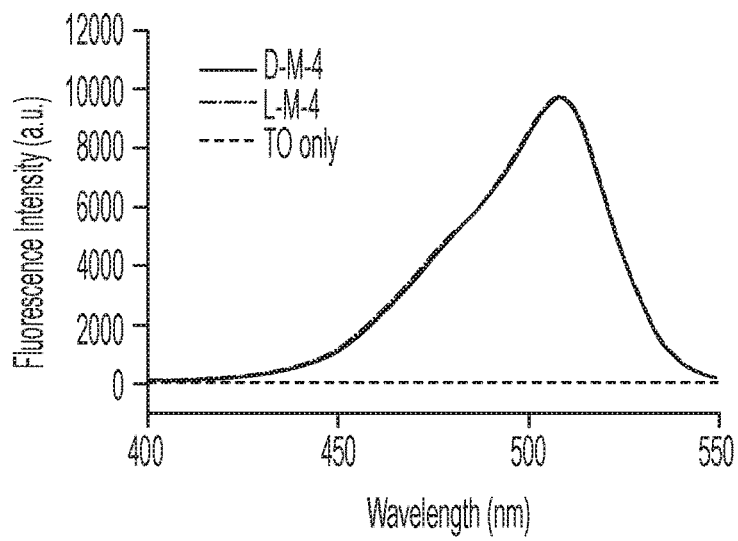
FIG. 10B shows fluorescence spectra of D-M-4, L-M-4 and TO dye. Buffer conditions are the same as described in FIG. 10A.
Figure 11A:
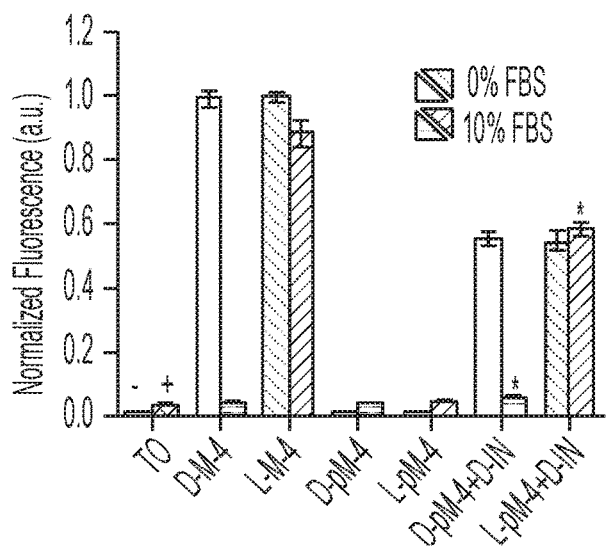
FIG. 11A shows fluorescence activation of pM-4 under various conditions. Reactions contained 400 nM of the indicated aptamer complex (M-4 or pM-4), 0 or 400 nM D-IN, 400 nM TO dye, 100 mM KCl, 0.5 mM MgCl$_2$, and 10 mM HEPES (pH 7.4) and were carried out at 37° C. for 20 min. The presence or absence of 10% FBS is indicated by shading. For reference, the fluorescence of TO alone in the presence (+) or absence (−) of 10% FBS is also shown.
Figure 13:
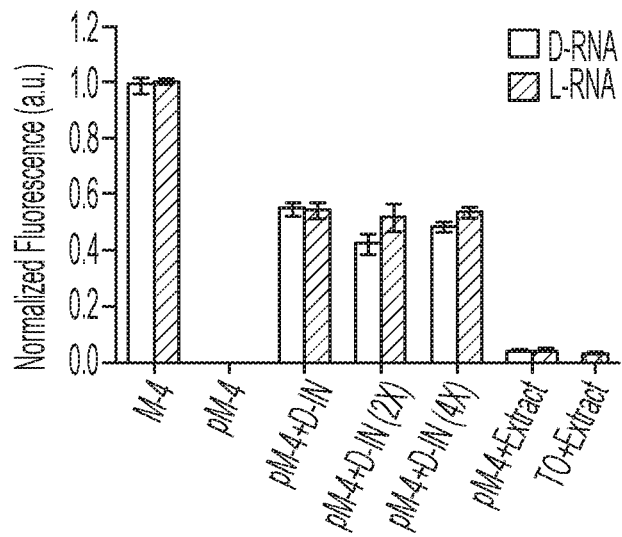
FIG. 13 illustrates in vitro characterization of pM-4 sensor activation. Fluorescence activation of D-pM-4 and L-pM-4 in the presence of either excess D-IN or nonspecific RNA from HeLa cells. Reaction mixtures contained the 400 nM of either M-4 or pM-4, either 0, 400, 800, or 1600 nM D-IN, 400 nM TO, 100 mM KCl, 0.5 mM MgCl$_2$, and 10 mM HEPES (pH 7.4) and were incubated for 20 minutes at 37° C. Total RNA extract from HeLa cells (80 µg/mL) was added to the indicated experiments.

Next, the L-RNA version of M-4 (L-M-4) was synthesized, which exhibited mirror image symmetry with D-M-4 when measured by circular dichroism (CD) spectroscopy, as shown in FIG. 10A. In the absence of the PNA blocking strand, both D-M-4 and L-M-4 activated the fluorescence of TO to a similar extent, confirming that L-RNA versions of fluorogenic aptamers retain their activity, as shown in FIG. 10B and FIG. 11A. Likewise, in the presence of the PNA blocking strand, both P1:M-4 complexes (D-pM-4 and L-pM-4) were unable to activate TO fluorescence, indicating that the achiral PNA strand hybridized efficiently to both D-RNA and L-RNA versions of the aptamer. Treatment of both D-pM-4 and L-pM-4 complexes with an equimolar amount of D-IN RNA resulted in the recovery of approximately 55% of the fluorescent signal observed for the unblocked aptamers within 20 minutes, illustrated in FIG. 11A. Proper operation of the sensor in the presence of D-IN was further validated by native gel electrophoresis. Even in the presence of excess D-IN, the fluorescence signal of the pM-4 sensor relative to free M-4 aptamer was unable to fully activate, as shown in FIG. 13. Given the unique mechanism of strand-displacement, which requires helical inversion through domains 2 and 3, it is possible that a fraction of the M-4 aptamer remains improperly folded upon release of the PNA blocking strand. Nevertheless, the >50-fold fluorescence enhancement upon the addition of D-IN (i.e., miRNA-155) to D-pM-4 and L-pM-4 was deemed more than sufficient for subsequent intracellular studies. In contrast, only a minor fluorescence signal was detected for both D-pM-4 and L-pM-4 complexes in the presence of excess nuclear RNAs (<5% of maximum), which was attributed to non-specific binding of the TO dye to the excess RNA rather than spurious sensor activation, as shown in FIG. 13. Taken together, these data indicate that the L-pM-4 sensor can rapidly and selectively detect D-miRNA-155.

In order to demonstrate the compatibility of L-pM-4 with complex biological environments, the behavior of both D-RNA and L-RNA versions of the sensor in the presence of 10% fetal bovine serum (FBS) was investigated. As expected, the D-M-4 Mango III aptamer was completely degraded within 5 minutes in the presence of 10% FBS, as determined by gel electrophoresis. In contrast, no degradation was observed for L-M-4 after 12 hours under the same conditions, which is consistent with the inability of protein nucleases to recognize L-RNA. Accordingly, L-M-4, but not D-M-4, was capable of enhancing the fluorescence of TO (~20-fold) in the presence of 10% FBS, shown in FIG. 11A.

Figure 11B:
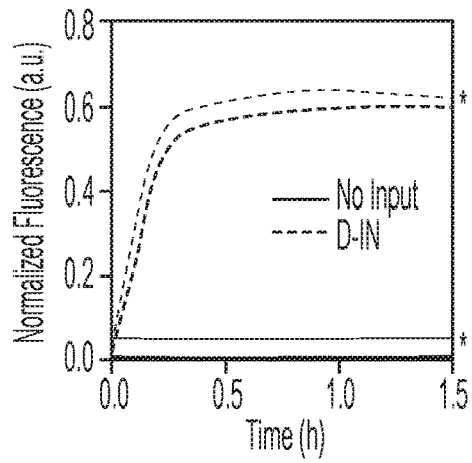
FIG. 11B illustrates fluorescence monitoring (Mango) of L-pM-4 activation in the absence of (solid line) or presence of (dashed line) 10% FBS. Reaction conditions were identical to those described in FIG. 11A. Fluorescence values in both FIG. 11A and FIG. 11B were normalized to the intensity of the unblocked Mango aptamer (D-M-4 or L-M-4). The asterisk indicates use of a DNA version of the input (D-IN).

Upon binding of L-M-4 to the PNA blocking strand, which itself is resistant to enzymatic degradation, a sustained absence of a fluorescence signal was observed, indicating that the L-pM-4 probe complex remained intact in the presence of FBS, illustrated in FIG. 11A and FIG. 11B. Treatment of L-pM-4 with D-IN resulted in a ~14-fold fluorescence enhancement of TO within 20 minutes, illustrated in FIG. 11A and FIG. 11B. In fact, fluorescence data obtained for the L-pM-4 probe in the presence of 10% FBS closely mirrored the data obtained in the absence of FBS, illustrated in FIG. 11A and FIG. 11B, demonstrating that complex biological matrixes do not interfere with the activity of the L-RNA sensor. Not surprisingly, attempts to detect the D-IN using the D-RNA version of the probe (D-pM-4) failed in the presence of 10% FBS, illustrated in FIG. 11A, highlighting advantages of L-RNA.

Figure 14:
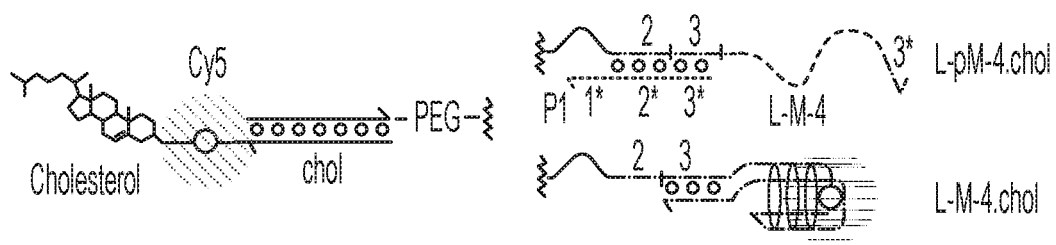
FIG. 14 illustrates self-delivery of the L-Mango sensor into live cells.
Figure 15:
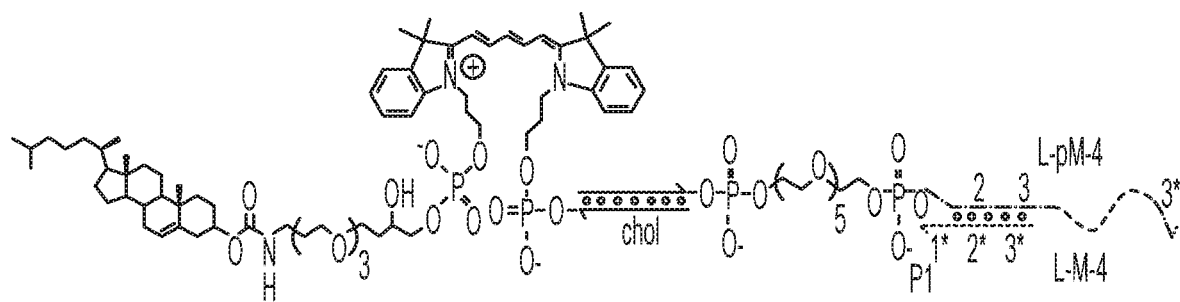
FIG. 15 shows a detailed schematic illustration of L-pM-4.chol sensor.

Having confirmed the biocompatibility of L-pM-4, attention was turned towards cellular delivery. Rather than relying on traditional transfection reagents (e.g., Lipofectamine) to deliver the probe into cells, which can have adverse effects on cell viability, a self-delivering strategy based on cholesterol conjugation was employed instead. Attachment of lipophilic molecules to oligonucleotides is a delivery strategy, which applies to the delivery of antisense oligonucleotides, siRNAs, and D-aptamers. As depicted in FIG. 14A, a short sequence of D-DNA was appended to the 5' end of the L-M-4 aptamer via a flexible polyethylene glycol (PEG) linker, to which a cholesterol-modified oligonucleotide was annealed, shown in FIG. 15. This "sticky bridge" approach was chosen because it offers the flexibility for attachment of other chemical moieties for future applications. The cholesterol-modified oligonucleotide (chol) was also labeled internally with a Cy5 fluorophore to enable ratiometric imaging for quantification of live cell studies. Disclosed herein, the self-delivering sensor complex will be referred to as L-pM-4.chol, whereas a similar complex without the PNA blocking strand will be referred to as L-M-4.chol, illustrated in FIG. 14A, which serves as a positive control for delivery. Incubation of HeLa cells with L-M-4.chol (no PNA) resulted in a gradual, time-dependent increase in both Mango and Cy5 fluorescence within the cytoplasm of these cells. Fluorescence microscopy imaging of HeLa cells was conducted following a 12 h incubation with 100 nM each L-M-4.chol and TO. Fluorescence imaging of the time-dependent cellular uptake of L-M-4.chol (unblocked sensor) into wild-type HeLa cells was also conducted. This not only showed that L-M-4.chol could perform efficient self-delivery without the need for transfection reagents, but also demonstrated, for the first time, that fluorogenic aptamers comprised of L-RNA are compatible with intracellular imaging applications.

Figure 16A:
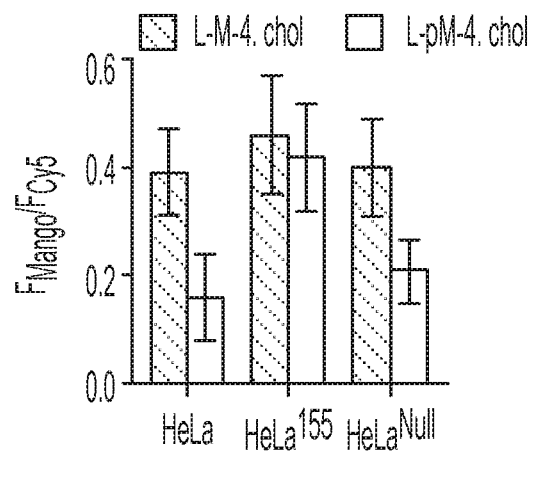
FIG. 16A shows mean fluorescence intensities ($F_{Mango}/F_{Cy5}$) in the above cell lines. Error bars represent the standard deviation from at least six images obtained from two separate experiments. Scale bar: 100 µm.
Figure 16B:
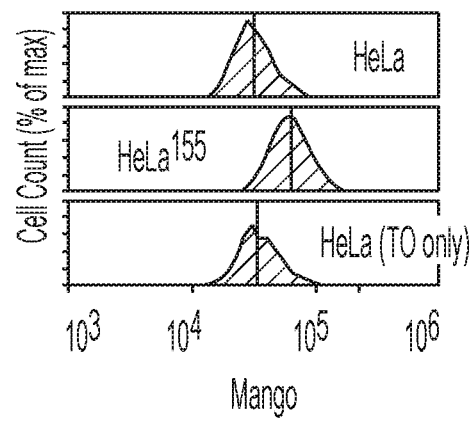
FIG. 16B illustrates flow cytometry histogram of HeLa cells treated with either L-pM-4.chol or TO alone (the line indicates the mean value).

Finally, the ability of the self-delivering L-pM-4.chol sensor to image miRNA-155 expression in living cells was tested, as shown in FIG. 16. For these experiments, a HeLa cell line stably expressing miRNA-155 (HeLa[155]) was generated, which showed an elevated expression level of miRNA-155 (>200-fold) relative to wild-type HeLa cells, illustrated in FIG. 12. Representative fluorescence microscopy imaging of different HeLa cell lines following a 12 hour incubation with L-pM-4.chol was conducted. Incubation of both HeLa cell lines with L-pM-4.chol resulted in an intense Cy5 signal in the cytosol, indicating that the L-pM-4.chol sensor was efficiently internalized into both cell types. However, the Mango fluorescence signal was brighter in HeLa[155] cells compared to wild-type HeLa cells, consistent with overexpression of miRNA-155 in HeLa[155] cells. Ratiometric quantification of these data, which was carried out by dividing the averaged fluorescence intensities of Mango and Cy5 ($F_{Mango}/F_{Cy5}$), revealed that ~2-fold more L-pM-4.chol sensors were activated within HeLa[155] cells as compared to wild-type HeLa cells, illustrated in FIG. 16A. Treatment of HeLa[155] cells with either L-pM-4.chol or the unblocked sensor lacking the PNA strand (L-M-4.chol) resulted in a similar $F_{Mango}/F_{Cy5}$ ratio, indicating that nearly all L-pM-4.chol sensor molecules were activated within these cells. In contrast, no significant difference in fluorescence activation of L-pM-4.chol was observed between wild-type HeLa cells and a third HeLa cell line stably expressing a null vector lacking the miRNA-155 gene (HeLa[Null]). The increased mango signal in HeLa[155] cells relative to wild-type HeLa cells was further confirmed by flow cytometry, illustrated in FIG. 16B. Together, these results indicated that the L-pM-4.chol sensor successfully activated a fluorescent signal in response to elevated miRNA-155 expression levels in live cells. It was noted that treatment of wild-type HeLa cells with TO alone resulted in a fluorescence signal that was nearly equivalent to the same cells treated with L-pM-4.chol, shown in FIG. 16B, suggesting that the TO dye itself was responsible for the majority of background fluorescence in the absence of miRNA-155 expression.

In summary, presented in detail above, is the development of fluorogenic aptamer-based sensor comprised of L-RNA. The sensor exhibited excellent stability in both serum and living cells, where it was successfully employed to image the expression of miRNA-155. This is the first time an endogenously expressed nucleic acid has been sequence-specifically interfaced with a synthetic L-oligonucleotide in a living system. Thus, the present disclosure provides a starting point for interfacing more complex L-oligonucleotide-based circuits with living cells and organisms for applications in bioengineering, synthetic biology, and clinical diagnostics. Moreover, the results presented herein show that fluorogenic aptamers comprised of L-RNA are compatible with complex biological environments and live-cell imaging, thereby greatly expanding the utility of this class of bio-imaging tools. Taken together, the present disclosure signifies several major advances in the area of intercellular biosensing, which have a far-reaching impact on how nucleic acid-based sensors are designed and implemented.

Although various embodiments of the present disclosure have been illustrated in the accompanying Drawings and described in the foregoing Detailed Description, it will be understood that the present disclosure is not limited to the embodiments disclosed herein, but is capable of numerous rearrangements, modifications, and substitutions without departing from the spirit of the disclosure as set forth herein.

The term "substantially" is defined as largely but not necessarily wholly what is specified, as understood by a person of ordinary skill in the art. In any disclosed embodiment, the terms "substantially," "approximately," "generally," and "about" may be substituted with "within [a percentage] of" what is specified, where the percentage includes 0.1, 1, 5, and 10 percent.

The foregoing outlines features of several embodiments so that those skilled in the art may better understand the aspects of the disclosure. Those skilled in the art should appreciate that they may readily use the disclosure as a basis for designing or modifying other processes and structures for carrying out the same purposes and/or achieving the same advantages of the embodiments introduced herein. Those skilled in the art should also realize that such equivalent constructions do not depart from the spirit and scope of the disclosure, and that they may make various changes, substitutions, and alterations herein without departing from the spirit and scope of the disclosure. The scope of the invention should be determined only by the language of the claims that follow. The term "comprising" within the claims is intended to mean "including at least" such that the recited listing of elements in a claim are an open group. The terms "a," "an," and other singular terms are intended to include the plural forms thereof unless specifically excluded.

What is claimed is:

1. A chimeric DNA/PNA complex comprising:
   an input strand, wherein the input strand binds to the chimeric DNA/PNA complex and releases the DNA strand wherein the released DNA strand has an activated domain; and
   reporter complex that binds to the activated domain on the released DNA strand.

2. The chimeric DNA/PNA complex of claim 1, wherein the reporter complex is selected from the group consisting of D-R2, L-R2, Cy3, Cy5, Cy3/BHQ2, Cy5/BHQ3, and combinations thereof.

3. The chimeric DNA/PNA complex of claim 1, wherein the input strand has an opposite chirality as the DNA in the chimeric DNA/PNA complex.

4. The chimeric DNA/PNA complex of claim 1, wherein the input strand is selected from the group consisting of DNA, RNA, DNA or RNA analogs, and combinations thereof.

5. The chimeric DNA/PNA complex of claim 4, wherein the input strand is RNA and has an opposite chirality as the DNA in the DNA/PNA complex.

6. The chimeric DNA/PNA complex of claim 4, wherein the input strand is DNA and has an opposite chirality as the DNA in the DNA/PNA complex.

* * * * *